(12) United States Patent
Bai et al.

(10) Patent No.: US 9,487,470 B2
(45) Date of Patent: Nov. 8, 2016

(54) 4-((SUBSTITUTED PHENYL) DIFLUOROMETHYL) PHENOXY CARBOXYLIC ACID DERIVATIVE, AND PREPARATION METHOD AND USES THEREOF

(71) Applicant: Zhejiang Hisun Pharmaceutical Co., Ltd., Taizhou (CN)

(72) Inventors: Hua Bai, Taizhou (CN); Jian Hong, Zhejiang (CN); Lifeng Cai, Zhejiang (CN); Hegeng Wei, Zhejiang (CN); Xiaoyu Liu, Taizhou (CN); Xiaohe Zheng, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 8 days.

(21) Appl. No.: 14/396,455

(22) PCT Filed: Apr. 25, 2013

(86) PCT No.: PCT/CN2013/074739
§ 371 (c)(1),
(2) Date: Oct. 23, 2014

(87) PCT Pub. No.: WO2013/159724
PCT Pub. Date: Oct. 31, 2013

(65) Prior Publication Data
US 2015/0119458 A1 Apr. 30, 2015

(30) Foreign Application Priority Data
Apr. 26, 2012 (CN) .......................... 2012 1 0125154

(51) Int. Cl.
| | | |
|---|---|---|
| *C07C 69/712* | (2006.01) |
| *C07C 59/68* | (2006.01) |
| *C07C 51/363* | (2006.01) |
| *C07C 59/135* | (2006.01) |
| *C07C 67/307* | (2006.01) |
| *C07C 69/78* | (2006.01) |
| *C07C 319/16* | (2006.01) |
| *C07C 323/16* | (2006.01) |
| *C07C 323/56* | (2006.01) |
| *C07D 307/33* | (2006.01) |
| *C07C 69/94* | (2006.01) |

(52) U.S. Cl.
CPC .......... *C07C 69/712* (2013.01); *C07C 51/363* (2013.01); *C07C 59/135* (2013.01); *C07C 59/68* (2013.01); *C07C 67/307* (2013.01); *C07C 69/78* (2013.01); *C07C 69/94* (2013.01); *C07C 319/16* (2013.01); *C07C 323/16* (2013.01); *C07C 323/56* (2013.01); *C07D 307/33* (2013.01)

(58) Field of Classification Search
CPC ... C07C 69/712; C07C 59/68; C07C 59/135; C07C 51/363
See application file for complete search history.

(56) References Cited

U.S. PATENT DOCUMENTS 4,058,552 A 11/1977 Mieville
4,739,101 A 4/1988 Bourgogne et al.

FOREIGN PATENT DOCUMENTS

| CN | 102659570 A | 9/2012 |
| JP | 2004359630 A | 12/2004 |
| WO | 0239983 A2 | 5/2002 |

OTHER PUBLICATIONS

Evans et al 'PPARs and the complex journey to obesity' Nature Medicine, 10(4), p. 1-7, 2004.*
Dehmlow et al., "Synthesis and Structure-Activity Studies of Novel Orally Active Non-Terpenoic 2,3-Oxidosqualene Cyclase Inhibitors", J. Med. Chem., 2003, 46, 3354-3370.
International Search Report for Application No. PCT/CN2013/074739 dated Aug. 8, 2013.
Practical Pharmacy and Clinical Remedies, 2005, 8, 35-36 (English translation of Abstract provided herewith).

* cited by examiner

*Primary Examiner* — Wu-Cheng Winston Shen
*Assistant Examiner* — Christopher R Stone
(74) *Attorney, Agent, or Firm* — Lerner, David, Littenberg, Krumholz & Mentlik, LLP

(57) ABSTRACT

The present invention discloses a 4-((substituted phenyl) difluoromethyl)phenoxycarboxylic acid derivative and preparation process and use thereof. More specifically, the present invention relates to a compound of the following formula I, which is defined in the specification. The compounds according to the present invention can be used as PPAR agonists, and demonstrates a strong effect on reducing the levels of total cholesterol (TC), triglyceride (TG), and low density lipoprotein cholesterol (LDL-C) in blood plasma, and thus the compound according to the present invention can be used in the preparation of a medicament for treating or preventing hyperlipoidemia or cardio-cerebrovascular diseases caused by hyperlipoidemia, such as diabetes, atherosclerosis, stroke, coronary heart disease, etc. The present invention also relates to a novel intermediate compound for the preparation of the compound of formula I and preparation method thereof.

19 Claims, No Drawings

4-((SUBSTITUTED PHENYL) DIFLUOROMETHYL) PHENOXY CARBOXYLIC ACID DERIVATIVE, AND PREPARATION METHOD AND USES THEREOF

CROSS-REFERENCE TO RELATED APPLICATIONS

The present application is a national phase entry under 35 U.S.C. §371 of International Application No. PCT/CN2013/074739, filed on Apr. 25, 2013, published in Chinese, which claims priority from Chinese Patent Application No. 201210125154.4, filed Apr. 26, 2012, the disclosures which are hereby incorporated herein by reference.

FIELD OF THE INVENTION

The present invention relates to 4-((substituted phenyl) difluoromethyl)phenoxycarboxylic acid derivatives and preparation method thereof, also relates to the use of the 4-((substituted phenyl)difluoromethyl)phenoxycarboxylic acid derivatives according to the present invention in the preparation of a medicament for treating or preventing cardio-cerebrovascular diseases caused by hyperlipoidemia, such as diabetes, atherosclerosis, stroke, coronary heart disease, etc. The present invention also relates to a novel intermediate compound of such novel compounds, and preparation method thereof.

BACKGROUND OF THE INVENTION

Cardiovascular diseases are most common and serious diseases that threaten the health of human, especially middle-aged and elder human. Dyslipidemia, especially hyperlipoidemia, is the most risky factor of atherosclerosis, coronary heart disease, and other cardio-cerebrovascular diseases. With the aging of population, the increasing of fat intake by human, and the decreasing of exercising, the incidence of hyperlipoidemia and its complication are increasing and the age of onset of such disease tends to decrease, which threatens the health and quality of life of human seriously.

Lipid-regulating drugs can decrease the incidence and mortality of such diseases, and have positive effect and prolonged influence on the prevention and treatment of cardio-cerebrovascular diseases. Therefore, the research and development of antihyperlipidemics with high efficiency and safety has been a major topic in the field of medicine for a long time.

For the identification of dyslipidemia, the levels of blood total cholesterol (TC), triglyceride (TG), and high density lipoprotein cholesterol (HDL-C) are conventionally analyzed in clinical, and it is conventionally classified into 3 types, i.e. hypercholesterolemia, hypertriglyceridemia, and combined dyslipidemia. Current clinical and developing antihyperlipidemics are classified, according to their mechanisms and chemical structures, statins, nicotinic acids, fibrates, bile acid sequestrants, polyenes, and novel antihyperlipidemics and various composite formulations. Their treatment scheme is reducing the levels of blood TC, TG, and low density lipoprotein cholesterol (LDL-C) level and increasing the level of HDL-C.

Fibrates and their derivatives, as PPAR agonists, are major commercially drugs being used for lowering triglyceride, among others, fenofibrate is representative. According to the reports of U.S. Pat. No. 4,058,552; Practical Pharmacy and Clinical Remedies, 2005, 8, 35-36; and WO02/39983, it has poor bioavailability, and larger dosage is required for achieving desired effects. Furthermore, daily multiple-dose administration is required, and food is required to regulate its bioavailability. Meanwhile, it also has significant adverse effects to gastrointestinal tract.

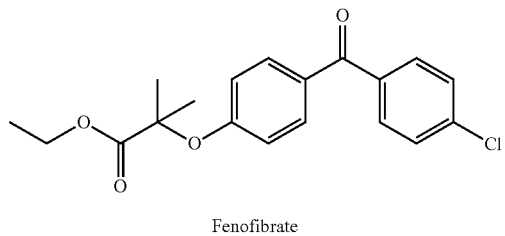 [SMILES: CCOC(=O)C(C)(C)Oc1ccc(C(=O)c2ccc(Cl)cc2)cc1]

Fenofibrate

Therefore, how to develop an antihyperlipidemics for treating hyperlipoidemia with high efficiency has always been a major problem to be solved by researchers.

DETAILED DESCRIPTION

Unless otherwise indicated, the scientific terms and technical terms have the meanings as known by the person skilled in the art.

The terms "Ca-Cb" alkyl, alkoxy, alkoxyacyl, aryl, aryloxy, or aryloxyacyl means that these groups can comprise any integer from "a" to "b", including a and b, of carbon atoms. A numerical range, e.g. "C1-C6", refers to every integer within the specified range, including 1 carbon atom, 2 carbon atoms, 3 carbon atoms, 4 carbon atoms, 5 carbon atoms, and 6 carbon atoms; a numerical range, e.g. "C6-C10", refers to every integer within the specified range, including 6 carbon atoms, 7 carbon atoms, 8 carbon atoms, 9 carbon atoms, and 10 carbon atoms. Therefore, e.g. "C1-C6 alkyl" groups refers to all alkyl groups having 1, 2, 3, 4, 5, and 6 carbon atoms, and "C6-C10 aryl" groups refers to all aryl groups having 6, 7, 8, 9, and 10 carbon atoms.

The present invention relates to a type of 4-((substituted phenyl)difluoromethyl)phenoxy carboxylic acid derivatives of formula I, capable of lowing blood lipid, or pharmaceutically acceptable salts or solvates thereof

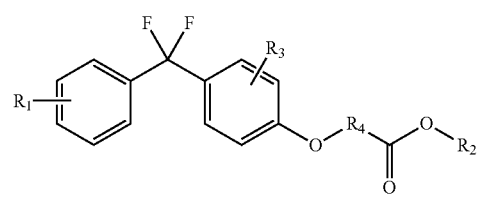

I

Wherein, $R_1$ can be hydrogen, fluoro, chloro, bromo, trifluoromethyl, substituted or unsubstituted linear or branched C1-C6 alkoxyacyl, substituted or unsubstituted C6-C10 aryloxyacyl, substituted or unsubstituted linear or branched C1-C6 alkyl, substituted or unsubstituted C6-C10 aryl, substituted or unsubstituted linear or branched C1-C6 alkoxy, substituted or unsubstituted C6-C10 aryloxy, substituted or unsubstituted linear or branched C1-C6 alkyl ester; preferably, $R_1$ is hydrogen, fluoro, chloro, bromo, trifluoromethyl, methyl, methoxy, methoxyacyl, or isopropyl 2-O-2-methylpropioate;

$R_2$ can be hydrogen, substituted or unsubstituted linear or branched C1-C6 alkyl, or substituted or unsubstituted C6-C10 aryl; preferably, $R_2$ is hydrogen, methyl, ethyl, propyl, isopropyl, or benzyl.

$R_3$ is hydrogen, fluoro, chloro, bromo, or substituted or unsubstituted linear or branched C1-C6 alkyl; preferably, R3 is hydrogen, fluoro, chloro, methyl, or ethyl.

The position of $R_1$ on the benzene ring can be ortho-position, para-position or meta-position to difluoromethylene group;

The position of $R_3$ on the benzene ring can be ortho-position or meta-position to difluoromethylene group.

$R_4$ is substituted or unsubstituted C1-C6 alkyl;

Said substitutent can be selected from fluoro, chloro, bromo, difluoromethyl, trifluoromethyl, difluoromethoxy, carboxyl, carbonyl, ester group, aldehyde group, hydroxyl, acetal, ether, thioether, or amine.

The above mentioned compound of formula I is selected from the following compounds:

Isopropyl 2-(4-((4-chlorophenyl)difluoromethyl)phenoxy)-2-methylpropionate;
isopropyl 2-(4-((4-bromophenyl)difluoromethyl)phenoxy)-2-methylpropionate;
isopropyl 2-(4-((4-fluorophenyl)difluoromethyl)phenoxy)-2-methylpropionate;
isopropyl 2-(4-((4-trifluoromethylphenyl)difluoromethyl)phenoxy)-2-methylpropionate;
isopropyl 2-(4-(phenyldifluoromethyl)phenoxy)-2-methylpropionate;
isopropyl 2-(4-((4-methylphenyl)difluoromethyl)phenoxy)-2-methylpropionate;
isopropyl 2-(4-((4-methoxyphenyl)difluoromethyl)phenoxy)-2-methylpropionate;
isopropyl 2-(4-((3-chlorophenyl)difluoromethyl)phenoxy)-2-methylpropionate;
isopropyl 2-(4-((3-methylphenyl)difluoromethyl)phenoxy)-2-methylpropionate;
isopropyl 2-(4-((3-trifluoromethylphenyl)difluoromethyl)phenoxy)-2-methylpropionate;
isopropyl 2-(4-((2-chlorophenyl)difluoromethyl)phenoxy)-2-methylpropionate;
isopropyl 2-(4-((2-methylphenyl)difluoromethyl)phenoxy)-2-methylpropionate;
isopropyl 2-(4-((2-trifluoromethylphenyl)difluoromethyl)phenoxy)-2-methylpropionate;
isopropyl 2-(4-((4-methoxyacylphenyl)difluoromethyl)phenoxy)-2-methylpropionate;
bis-(isopropyl 2-methylpropionate-2-oxyphenyl-4-)-difluoromethane;
isopropyl 2-(4-((4-chlorophenyl)difluoromethyl)-3-methylphenoxy)-2-methylpropionate;
isopropyl 2-(4-((4-chlorophenyl)difluoromethyl)-2-chlorophenoxy)-2-methylpropionate;
benzyl 2-(4-((4-chlorophenyl)difluoromethyl)phenoxy)-acetate;
ethyl 2-(4-((4-chlorophenyl)difluoromethyl)phenoxy) butyrate;
methyl 2-(4-((4-chlorophenyl)difluoromethyl)phenoxy) propionate;
ethyl 4-(4-((4-chlorophenyl)difluoromethyl)phenoxy) butyrate;
sodium 2-(4-((4-chlorophenyl)difluoromethyl)phenoxy)-2-methylpropionate;
2-(4-((4-chlorophenyl)difluoromethyl)phenoxy)-2-methylpropionic acid;
methyl 2-(4-((4-chlorophenyl)difluoromethyl)phenoxy)-4-hydroxy-butyrate;
3-(4-((4-chlorophenyl)difluoromethyl)phenoxy)-dihydrofuran-2(3H)-one;
isopropyl 2-(4-((4-chlorophenyl)difluoromethyl)-2-bromophenoxy)-2-methylpropionate;
isopropyl 2-(4-((4-trifluoromethylphenyl)difluoromethyl)-2-bromophenoxy)-2-methylpropionate;
isopropyl 2-(4-((4-methoxyacylphenyl)difluoromethyl)-2-bromophenoxy)-2-methylpropionate.

Said salt refers to the salt with corresponding base, such as alkali metal salt, alkali earth metal salt, in particular sodium salt, potassium salt, lithium salt, magnesium salt, calcium salt, etc., in the case that hydroxy group or carboxyl group presents in the compound of formula I.

The solvate of the compound of formula I according to the present invention refers to its hydrate or solvate with an organic solvent.

The present invention also relates to a pharmaceutical composition, comprising an effective dosage of the compound of formula I or a pharmaceutically acceptable salt or solvate thereof.

Use of the compound of formula I or a pharmaceutically acceptable salt or solvate thereof in the preparation of a medicament for treating or preventing diseases requiring the activation of human peroxisome proliferator-activated receptor in its treatment and prevention.

Use of the compound of formula I or a pharmaceutically acceptable salt or solvate thereof in the preparation of a medicament for treating or preventing hyperlipoidemia or a disease caused by hyperlipoidemia, including but not limited to cardio-cerebrovascular diseases, e.g. diabetes, atherosclerosis, stroke, coronary heart disease, etc.

The pharmaceutical composition of the compound of formula I consists of the compound of formula I and pharmaceutical adjuvants.

Such adjuvants for pharmaceutical composition refer to the adjuvants that have been approved by pharmaceutical administrations and comply with the standard of pharmaceutical adjuvants. Such adjuvants include fillers, diluents, adhesives, glidants, suspending agents, lubricants, disintegrants, cosolvents, buffers, preservatives, antioxidants, flavoring agents, thickening agents, colorants, emulsifiers, etc. They have no activity in human body, and have neither therapeutical effects nor toxicity.

Among the above mentioned adjuvants, the diluents can be selected from one or more of the following substances: starch, modified starch, sugarcane, lactose monohydrate, lactose anhydrate, glucose, mannitose, and microcrystalline cellulose of various specifications, such as Avicel™PH101, Avicel™PH102, Avicel™PH112, etc.

Among the above mentioned adjuvants, the adhesives can be selected from one of the following substances: hydroxypropylmethyl cellulose, pregelatinized starch, povidone (polyvinylpyrrolidone), carboxymethylcellulose and its derivatives, methyl cellulose, ethyl cellulose, starch, sugar, etc., preferably hydroxypropylmethyl cellulose, pregelatinized starch and povidone.

Among the above mentioned adjuvants, the glidants can be selected from one or more of the following substances: micronized silica gel.

Among the above mentioned adjuvants, the lubricants can be selected from one or more of the following substances: magnesium stearate, talc powder, hydrogenated vegetable oil type I.

Among the above mentioned adjuvants, the suspending agents can be selected from one or more of the following substances: glutin, pectin, gum Arabic, sodium alginate, methyl cellulose, ethyl cellulose, hydroxypropyl cellulose, carboxymethyl cellulose, sodium carboxymethyl cellulose, and methylcellulose.

Among the above mentioned adjuvants, the disintegrants can be selected from one or more of the following substances: starch, low substituted hydroxypropyl cellulose, sodium carboxymethyl starch, calcium carboxymethyl cellulose, crosslinked povidone, crosslinked cellulose, and crosslinked sodium carboxymethyl cellulose.

Among the above mentioned adjuvants, the cosolvents can be selected from one or more of the following substances: Spans, Tweens, polyethylene glycols, soybean lecithins, etc.

The above mentioned pharmaceutical composition can be administered in conventional dosage forms, preferably, in any of the following oral formulations: 1. blank tablets, 2. film coated tablets, 3. sugar coated tablets, 4. enteric coated tablets, 5. dispersible tablets, 6. capsules, 7. granules, 8. suspensions, and 9. solutions.

The above mentioned pharmaceutical composition and dosage forms can be prepared according to known processes.

The present invention discloses a process for the preparation of the compound of formula I, comprising reacting the compound according to the following formula II with an oxidant and a fluorination reagent to obtain the compound of formula I,

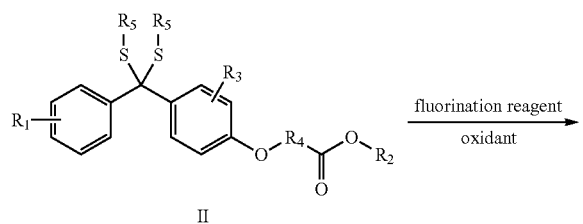

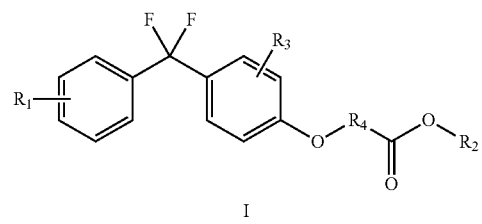

I

Wherein $R_1$, $R_2$, $R_3$, and $R_4$ are as defined in the compound of formula I, $R_5$ can be absent, i.e. in the form of thiocarbonyl, or is a linear or branched C1-C6 alkyl, alkyl-substituted or unsubstituted aryl, alternatively, two $R_5$ groups bond with each other and form a 5-7 member ring, together with two sulfur atoms and a carbon atom linking the two sulfur atoms.

Wherein, the fluorination reagent is selected from nucleophilic fluorination reagent, and can be selected from diethylaminosulfur trifluoride, bis(2-methoxyethyl)aminesulfur trifluoride, dimethylaminosulfur trifluoride, pyridine hydrofluoride, triethylamine hydrofluoride, sulfur tetrafluoride, hydrogen fluoride, potassium fluoride, silver fluoride, strontium fluoride, N-fluorodibenzenesulfonimide, dimethylaminosulfur trifluoride, morpholinosulfur trifluoride, 2,2-difluoro-1,3-dimethylimidazoline, 1-fluoro-2,6-dichloropyridine tetrafluoroborate, 1-fluoro-2,4,6-trimethylpyridine triflate, tetrabutylammonium hydrofluoride, hexafluoropropylene-diethylamine complex, difluoroiodotoluene, and N,N-diisopropylethylamine trihydrofluoride. Meanwhile, an oxidant, such as bromosuccinimide, dibromantin, iodosuccinimide, liquid bromine, or iodine is added into the reaction and the reaction temperature is preferably controlled from −25° C. to 90° C.

The present invention also discloses an alternative process for the preparation of the compound according to formula I, comprising reacting the compound according to the following formula III with a fluorination reagent to obtain the compound of formula I

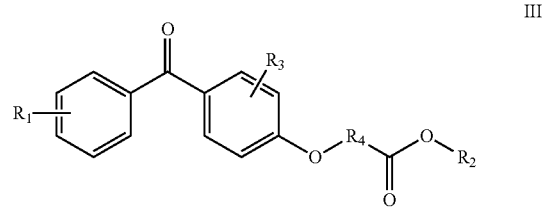

Wherein $R_1$, $R_2$, $R_3$, and $R_4$ are as defined in the compound of formula I.

The present invention also discloses a novel intermediate compound according to formula II

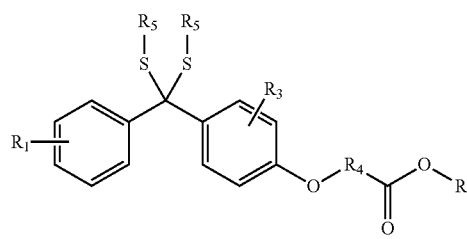

Wherein $R_1$, $R_2$, $R_3$, and $R_4$ are as defined in the compound of formula I, $R_5$ can be absent, i.e. only one S atom, which forms thiocarbonyl with the carbon atom between the two benzene rings, presents (i.e. the compound according to the following formula II-1), or is a linear or branched C1-C6 alkyl, alkyl-substituted or unsubstituted aryl, alternatively, two $R_5$ groups bond with each other and form a 5-7 member ring, together with two sulfur atoms and a carbon atom linking the two sulfur atoms

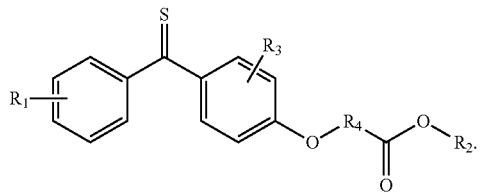

II-1

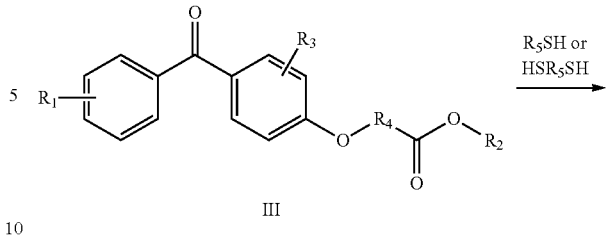

III

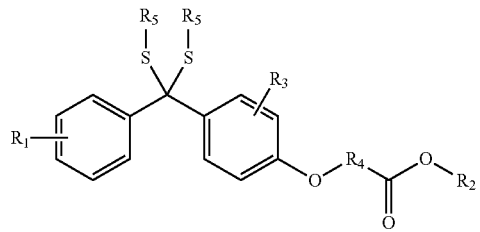

II

The above mentioned compound of formula II is selected from the following compounds:

isopropyl 2-(4-((4-chlorophenyl)bis(ethylmercapto)methyl) phenoxy)-2-methylpropionate;

isopropyl 2-(4-((4-bromophenyl)bis(ethylmercapto)methyl) phenoxy)-2-methylpropionate;

isopropyl 2-(4-((4-fluorophenyl)bis(ethylmercapto)methyl) phenoxy)-2-methylpropionate;

isopropyl 2-(4-((4-trifluoromethylphenyl)bis(ethylmercapto)methyl)phenoxy)-2-methylpropionate;

isopropyl 2-(4-(phenylbis(ethylmercapto)methyl)phenoxy)-2-methylpropionate;

isopropyl 2-(4-((4-methylphenyl)bis(ethylmercapto)methyl) phenoxy)-2-methylpropionate;

isopropyl 2-(4-((4-methoxyphenyl)bis(ethylmercapto) methyl)phenoxy)-2-methylpropionate;

isopropyl 2-(4-((3-chlorophenyl)bis(ethylmercapto)methyl) phenoxy)-2-methylpropionate;

isopropyl 2-(4-((3-methylphenyl)bis(ethylmercapto) fluoromethyl)phenoxy)-2-methylpropionate;

isopropyl 2-(4-((3-trifluoromethylphenyl)bis(ethylmercapto)methyl)phenoxy)-2-methylpropionate;

isopropyl 2-(4-((2-chlorophenyl)bis(ethylmercapto)methyl) phenoxy)-2-methylpropionate;

isopropyl 2-(4-((2-methylphenyl)bis(ethylmercapto)methyl) phenoxy)-2-methylpropionate;

isopropyl 2-(4-((2-trifluoromethylphenyl)bis(ethylmercapto)methyl)phenoxy)-2-methylpropionate;

isopropyl 2-(4-((4-methoxyacylphenyl)bis(ethylmercapto) methyl)phenoxy)-2-methylpropionate;

bis-(isopropyl 2-methylpropionate-2-oxyphenyl-4-)-bis(ethylmercapto)methane;

isopropyl 2-(4-((4-chlorophenyl)bis(ethylmercapto) methyl)-3-methylphenoxy)-2-methylpropionate;

isopropyl 2-(4-((4-chlorophenyl)bis(ethylmercapto) methyl)-2-chlorophenoxy)-2-methylpropionate;

benzyl 2-(4-((4-chlorophenyl)bis(ethylmercapto)methyl) phenoxy)-acetate;

ethyl 2-(4-((4-chlorophenyl)bis(ethylmercapto)methyl)phenoxy)butyrate;

methyl 2-(4-((4-chlorophenyl)bis(ethylmercapto)methyl) phenoxy) propionate;

ethyl 4-(4-((4-chlorophenyl)bis(ethylmercapto)methyl)phenoxy)butyrate.

The present invention relates to a process for the preparation of the compound of formula II, comprising carrying out the following reaction between the compound of formula III and alkylthiol, arylthiol, or alkyldithiol, in the presence of a Lewis acid or a proton acid, wherein $R_1$, $R_2$, $R_3$, and $R_4$ are as defined in the compound of formula I, and $R_5$ can be linear or branched C1-C6 alkyl or alkyl-substituted or unsubstituted aryl, but cannot be absent.

Wherein the Lewis acid can be selected from boron trifluoride etherate, chlorotrimethylsilane, zinc triflate, magnesium triflate, copper triflate, scandium triflate, bismuth nitrate, ferric trichloride, indium trichloride, zinc dichloride, titanium tetrachloride, tellurium tetrachloride, zirconium tetrachloride, and cobaltous bromide; and the proton acid can be selected from p-toluenesulfonic acid, hydrochloric acid, and sulfuric acid; the reaction temperature is preferably controlled from −20° C. to 90° C.

Alternatively, when $R_1$, $R_2$, $R_3$, and $R_4$ are as defined in the compound of formula I, and $R_5$ is selected from absent, i.e. in the form of thiocarbonyl, the process is a reaction between the compound of formula III and Lawesson's reagent or phosphorus pentasulfide.

The compound of formula III can be obtained commercially. Alternatively, if chemical synthesis is required, the following process can be employed:

With reference to the process in J. Med. Chem., 2003, 46, 3354, 2-(4-($R_1$ substituted benzoyl)phenoxy)-carboxylic acid derivatives (III) can be obtained from the reaction between 2-phenoxy-carboxylic acid derivative (IV) and various $R_1$ substituted benzoyl chloride (V), by catalysis with various Lewis acids. Conventional Lewis acids catalyst include aluminum trichloride, boron trifluoride, tin tetrachloride, ferric trichloride, zinc dichloride, etc. The solvents include nitrobenzene, methylene dichloride, ethylene dichloride, etc. The reaction temperature is from 0° C. to the reflux temperature of the solvent.

Alternatively, with reference to the process in U.S. Pat. No. 4,739,101, 2-(4-($R_1$ substituted benzoyl)phenoxy)-carboxylic acid derivatives can also be obtained by the condensation of 4-($R_1$ substituted benzoyl) phenol (VI) and 2-substituted carboxylic acid derivatives (VII), under the effect of a base. Conventional bases include sodium hydroxide, potassium hydroxide, sodium carbonate, potassium carbonate, cesium carbonate, etc.

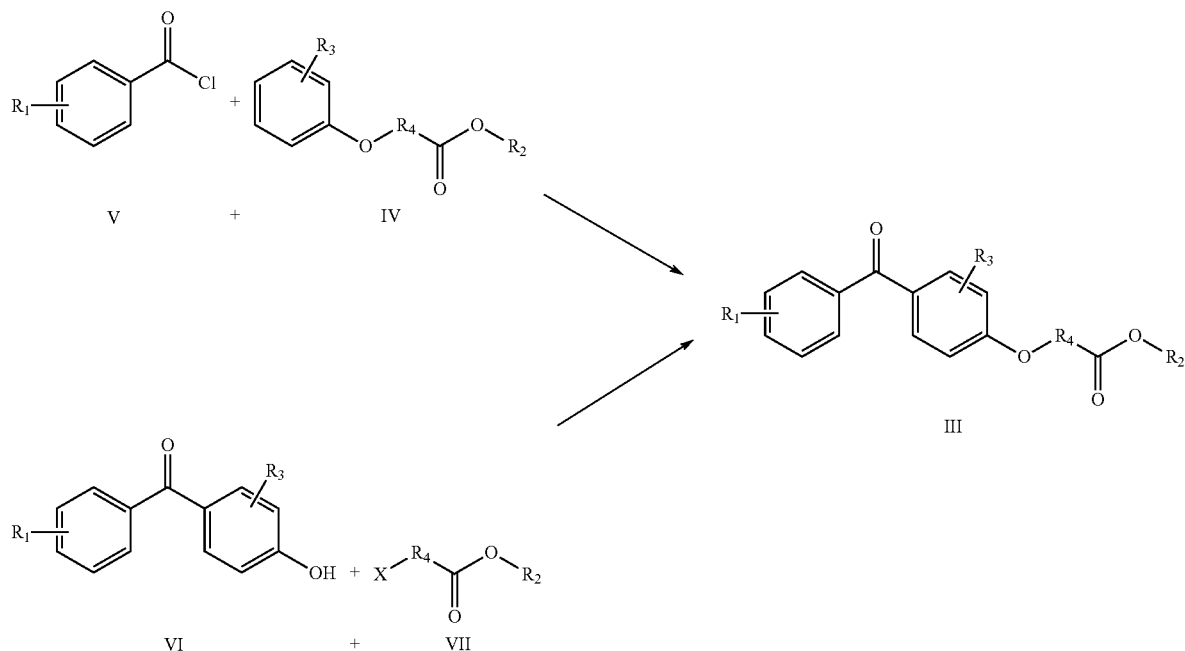

The compound according to the present invention can reduce the levels of total cholesterol (TC), triglyceride (TG), and low density lipoprotein cholesterol (LDL-C) in blood plasma, and thus the compound according to the present invention can be used in the treatment of cardio-cerebrovascular diseases caused by hyperlipoidemia, such as diabetes, atherosclerosis, stroke, coronary heart disease, etc.

EXAMPLES

The present invention will be further illustrated with reference to the following examples. The examples provide the preparation of representative compounds of formula I, and corresponding identification data of their structure, Unless indicated otherwise, the following examples are illustrative but do not intend to limit the present invention.

Unless indicated otherwise, the temperature in the following examples are represented as centigrade degree; unless indicated otherwise, all of the starting materials are obtained commercially. Unless indicated otherwise, the raw materials and reagents obtained commercially are used directly, without purification.

The NMR spectrum is determined using Bruker Avance III 400 device, the chemical shift is represented as ppm. Tetramethylsilane is used as the internal standard in $^1$H NMR, and CFCl$_3$ is used as the external standard in $^{19}$F NMR. The split peaks are represented as: s=singlet, d=doublet, t=triplet, q=quartet, and m=multiplet. If coupling constant is provided, its unit is Hz. The mass spectra is determined by Agilent 1200-6130 Quadrupole ESI.

All of the melting points are not corrected.

The following examples are provided for illustrating the synthesis process of a particular compound according to the present invention only, but do not intend to limit the synthesis process. The preparation of a compound, which is not listed in the following, can also adopt the following synthesis scheme and synthesis process, by selecting proper raw materials and making proper adjustment to the reaction conditions, if required (see Table 1).

Example 1

Preparation of isopropyl 2-(4-((4-chlorophenyl)difluoromethyl)phenoxy)-2-methylpropionate (HS003-004)

Step 1: Preparation of isopropyl 2-(4-((4-chlorophenyl)bis(ethylmercapto)methyl)phenoxy)-2-methylpropionate

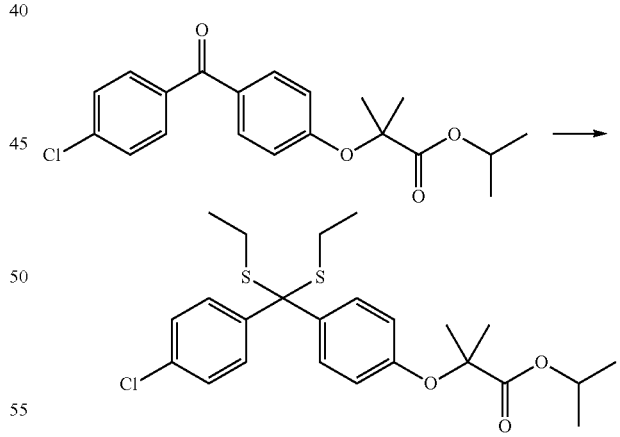

10 g of isopropyl 2-(4-(4-chlorobenzoyl)phenoxy)-2-methylpropionate was dissolved in 12 ml of ethanethiol, and then 8.7 ml of boron trifluoride etherate solution was slowly added dropwise at 0° C. After the dropping was complete, the stirring was continued for 1 h, until the reaction was complete. And then, it was quenched with saturated sodium bicarbonate, and extracted with ethyl acetate. The organic phase was successively washed with saturated sodium bicarbonate, water, and saturated saline solution, dried, and concentrated, and the crude product was subjected to column chromatography (petroleum ether:ethyl acetate/50:1), 12.4 g of the title product is obtained.

$^1$H NMR (400 MHz, CDCl$_3$) δ: 1.05 (t, J=7.6 Hz, 6H), 1.20 (d, J=6.4 Hz, 6H), 1.59 (s, 6H), 2.25-2.33 (m, 4H), 5.04-5.11 (m, 1H), 6.74 (d, J=8.8 Hz, 2H), 7.24 (d, J=8.8 Hz, 2H), 7.36 (d, J=8.8 Hz, 2H), 7.46 (d, J=8.8 Hz, 2H); ESI-MS (m/z): 489.5 (M+Na$^+$).

Step 2: Preparation of isopropyl 2-(4-((4-chlorophenyl)difluoromethyl)phenoxy)-2-methylpropionate

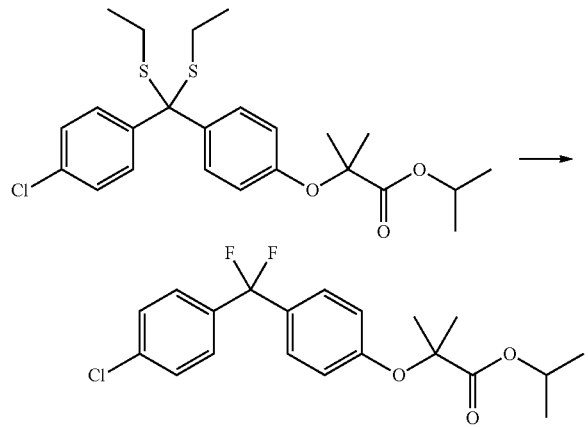

11.26 g of the above obtained isopropyl 2-(4-((4-chlorophenyl)bis(ethylmercapto)methyl)-phenoxy)-2-methylpropionate was dissolved in 20 ml of methylene dichloride, 8 g of bis(2-methoxyethyl)amine sulfur trifluoride was slowly added at 0° C. under the protection of argon, and then 10.68 g of bromosuccinimide was added. The stirring was continued at this temperature for 15 min, the reaction liquid was poured into 100 ml of ice cooled saturated sodium bicarbonate solution, and was extracted with 25 ml of methylene dichloride for 3 times. The organic phase was concentrated, washed with water, and dried, and then was subjected to column chromatography (petroleum ether:ethyl acetate/50:1), 9.0 g of an oily product is obtained.

$^1$H NMR (400 MHz, CDCl$_3$) δ: 1.22 (d, J=6.4 Hz, 6H), 1.63 (s, 6H), 5.10 (m, 1H), 6.86 (d, J=8.8 Hz, 2H), 7.35 (d, J=8.8 Hz, 2H), 7.39-7.46 (m, 4H); $^{13}$C NMR (100 MHz, CDCl$_3$) ppm 173.3, 157.0, 136.3 (t), 136.0, 130.3 (t), 128.6, 127.4 (t), 127.0 (t), 120.4 (t), 118.0, 79.2, 69.2, 25.4, 21.5; $^{19}$F NMR (376 MHz, CDCl3) δ: −86.3; ESI-MS (m/z): 405.0 (M+Na$^+$), 383.0 (M+H$^+$).

Example 2

Preparation of isopropyl 2-(4-((4-chlorophenyl)difluoromethyl)phenoxy)-2-methylpropionate (HS003-004)

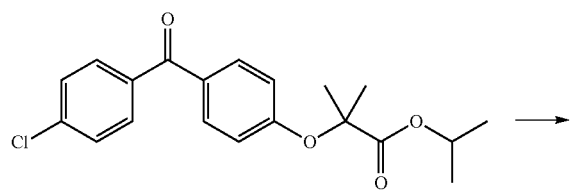

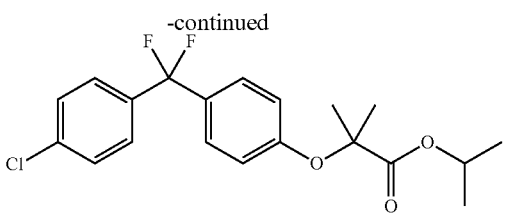

Bis(2-methoxyethyl)amine sulfur trifluoride was added into isopropyl 2-(4-(4-chlorobenzoyl)phenoxy)-2-methylpropionate under the protection of argon, the reaction system was heated to 90° C., and the reaction was kept for 24 h with stirring, the reaction liquid was cooled to room temperature, diluted with methylene dichloride, washed with saturated sodium bicarbonate solution and saturated saline solution, respectively, and the organic phase was dried and then subjected to column chromatography (petroleum ether:ethyl acetate/50:1), in order to obtain the desired compound isopropyl 2-(4-((4-chlorophenyl)difluoromethyl)phenoxy)-2-methylpropionate.

ESI-MS (m/z): 405.0 (M+Na$^+$), 383.0 (M+H$^+$).

The Following Compounds were Obtained According to the Synthesis Process of Example 1 or 2

Example 3

Preparation of isopropyl 2-(4-((4-bromobenzyl)difluoromethyl)phenoxy)-2-methylpropionate (HS003-005)

The following were obtained according to the process in example 1, using isopropyl 2-(4-((4-bromobenzoyl)phenoxy)-2-methylpropionate as the raw material.

Isopropyl 2-(4-((4-chlorophenyl)bis(ethylmercapto)methyl)phenoxy)-2-methylpropionate $^1$H NMR (400 MHz, CDCl$_3$) δ: 1.05 (t, J=7.6 Hz, 6H), 1.19 (d, J=6 Hz, 6H), 1.59 (s, 6H), 2.29 (d, J=7.6 Hz, 4H), 5.06-5.09 (m, 1H), 6.74 (d, J=8.4 Hz, 2H), 7.32-7.40 (m, 6H); ESI-MS (m/z): 533 (M+Na$^+$).

Isopropyl 2-(4-((4-bromophenyl)difluoromethyl)phenoxy)-2-methylpropionate $^1$H NMR (400 MHz, CDCl$_3$) δ: 1.22 (d, J=6 Hz, 6H), 1.63 (s, 6H), 5.10 (m, 1H), 6.86 (d, J=8.4 Hz, 2H), 7.29-7.39 (m, 4H), 7.56 (d, J=8.0 Hz, 2H); $^{13}$C NMR (100 MHz, CDCl$_3$) ppm 173.3, 157.1, 136.8 (t), 131.6, 130.2 (t), 127.7 (t), 127.0 (t), 124.3 (t), 120.4 (t), 118.1, 79.3, 69.2, 25.4, 21.5; ESI-MS (m/z): 449.0 (M+Na$^+$), 427.0 (M+H$^+$).

Example 4

Isopropyl 2-(4-((4-fluorophenyl)difluoromethyl)phenoxy)-2-methylpropionate (HS003-006)

The following were obtained according to the process in example 1, using isopropyl 2-(4-((4-fluorobenzoyl)phenoxy)-2-methylpropionate as the raw material.

Isopropyl 2-(4-((4-fluorophenyl)bis(ethylmercapto)methyl)phenoxy)-2-methylpropionate $^1$H NMR (400 MHz, CDCl$_3$) δ: 1.05 (t, J=7.4 Hz, 6H), 1.20 (d, J=6.4 Hz, 6H), 1.59 (s, 6H), 2.29 (q, J=7.4 Hz, 4H), 5.04-5.11 (m, 1H), 6.74 (d, J=8.8 Hz, 2H), 6.96 (t, J=8.4 Hz, 2H), 7.37 (d, J=8.8 Hz, 2H), 7.48-7.51 (m, 2H); ESI-MS (m/z): 473.5 (M+Na$^+$).

Isopropyl 2-(4-((4-fluorophenyl)difluoromethyl)phenoxy)-2-methylpropionate $^1$H NMR (400 MHz, CDCl$_3$) δ: 1.20 (d, J=6 Hz, 6H), 1.61 (s, 6H), 5.05-5.09 (m, 1H), 6.83 (d, J=8.4 Hz, 2H), 7.08 (t, J=8.4 Hz, 2H), 7.33 (d, J=8.8 Hz, 2H), 7.44-7.48 (m, 2H); $^{13}$C NMR (100 MHz, CDCl$_3$) ppm 173.4, 157.0, 133.8 (t), 130.5 (t), 128.1 (m), 127.0 (t), 120.5 (t), 118.1, 115.5, 115.3, 79.3, 69.1, 25.4, 21.5; ESI-MS (m/z): 389.0 (M+Na$^+$), 367.0 (M+H$^+$).

Example 5

Isopropyl 2-(4-((4-trifluoromethylphenyl)difluoromethyl)phenoxy)-2-methylpropionate (HS003-007)

The following were obtained according to the process in example 1, using isopropyl 2-(4-((4-trifluoromethylbenzoyl)phenoxy)-2-methylpropionate as the raw material.

Isopropyl 2-(4-((4-trifluoromethylphenyl)bis(ethylmercapto)methyl)phenoxy)-2-methylpropionate $^1$H NMR (400 MHz, CDCl$_3$) δ: 1.06 (t, J=7.6 Hz, 6H), 1.20 (d, J=6.4 Hz, 6H), 1.60 (s, 6H), 2.26-2.35 (m, 4H), 5.06-5.11 (m, 1H), 6.75 (d, J=8.4 Hz, 2H), 7.37 (d, J=8.8 Hz, 2H), 7.53 (d, J=8.0 Hz, 2H), 7.64 (d, J=8.0 Hz, 2H); ESI-MS (m/z): 501 (M+H$^+$).

Isopropyl 2-(4-((4-trifluoromethylphenyl)difluoromethyl)phenoxy)-2-methylpropionate $^1$H NMR (400 MHz, CDCl$_3$) δ: 1.20 (d, J=6 Hz, 6H), 1.61 (s, 6H), 5.04-5.10 (m, 1H), 6.84 (d, J=8.8 Hz, 2H), 7.33 (d, J=8.8 Hz, 2H), 7.61-7.69 (m, 4H); $^{13}$C NMR (100 MHz, CDCl$_3$) ppm 173.3, 157.2, 141.4 (t), 132.0 (q), 130.0 (t), 126.9 (t), 126.4 (t), 125.4 (t), 125.1, 120.1 (t), 118.1, 79.3, 69.2, 25.3, 21.5; ESI-MS (m/z): 439.0 (M+Na$^+$), 417.0 (M+H$^+$).

Example 6

Isopropyl 2-(4-(phenyldifluoromethyl)phenoxy)-2-methylpropionate (HS003-008)

The following were obtained according to the process in example 1, using isopropyl 2-(4-((4-benzoyl)phenoxy)-2-methylpropionate as the raw material.

Isopropyl 2-(4-(phenylbis(ethylmercapto)methyl)phenoxy)-2-methylpropionate $^1$H NMR (400 MHz, CDCl$_3$) δ: 1.03 (t, J=7.4 Hz, 6H), 1.19 (d, J=6 Hz, 6H), 1.59 (s, 6H), 2.31 (d, J=7.4 Hz, 4H), 5.06-5.11 (m, 1H), 6.74 (d, J=8.8 Hz, 2H), 7.19-7.29 (m, 3H), 7.39 (d, J=8.8 Hz, 2H), 7.51 (d, J=6.8 Hz, 2H); ESI-MS (m/z): 455.5 (M+H$^+$).

Isopropyl 2-(4-((4-phenyl)difluoromethyl)phenoxy)-2-methylpropionate $^1$H NMR (400 MHz, CDCl$_3$) δ: 1.19 (d, J=6.4 Hz, 6H), 1.61 (s, 6H), 5.03-5.10 (m, 1H), 6.83 (d, J=8.4 Hz, 2H), 7.35 (d, J=8.4 Hz, 2H), 7.38-7.41 (m, 3H), 7.47-7.49 (m, 2H); $^{13}$C NMR (100 MHz, CDCl$_3$) ppm 173.4, 157.0, 137.7 (t), 130.8 (t), 129.8, 128.3, 127.1 (t), 125.9 (t), 120.8 (t), 118.0, 79.2, 69.1, 25.4, 21.5; ESI-MS (m/z): 371.0 (M+Na$^+$), 349.0 (M+H$^+$).

Example 7

Isopropyl 2-(4-((4-methylphenyl)difluoromethyl)phenoxy)-2-methylpropionate (HS003-009)

The following were obtained according to the process in example 1, using isopropyl 2-(4-((4-methylbenzoyl)phenoxy)-2-methylpropionate as the raw material.

Isopropyl 2-(4-((4-methylphenyl)bis(ethylmercapto)methyl)phenoxy)-2-methylpropionate $^1$H NMR (400 MHz, CDCl$_3$) δ: 1.04 (t, J=7.4 Hz, 6H), 1.20 (d, J=6.4 Hz, 6H), 1.59 (s, 6H), 2.27-2.32 (m, 7H), 5.04-5.10 (m, 1H), 6.73 (d, J=8.4 Hz, 2H), 7.07 (d, J=7.6 Hz, 2H), 7.39 (d, J=7.6 Hz, 4H); ESI-MS (m/z): 469.5 (M+Na$^+$).

Isopropyl 2-(4-((4-methylphenyl)difluoromethyl)phenoxy)-2-methylpropionate $^1$H NMR (400 MHz, CDCl$_3$) δ: 1.20 (d, J=6 Hz, 6H), 1.60 (s, 6H), 2.37 (s, 3H), 5.05-5.08 (m, 1H), 6.82 (d, J=8.8 Hz, 2H), 7.20 (d, J=8 Hz, 2H), 7.33-7.37 (m, 4H); $^{13}$C NMR (100 MHz, CDCl$_3$) ppm 173.4, 156.8, 139.8, 134.9 (t), 131.1 (t), 129.0, 127.1 (t), 125.9 (t), 121.0 (t), 118.0, 79.2, 69.1, 25.4, 21.5, 21.3; ESI-MS (m/z): 385.1 (M+Na$^+$), 363.1 (M+H$^+$).

Example 8

Isopropyl 2-(4-((4-methoxyphenyl)difluoromethyl)phenoxy)-2-methylpropionate (HS003-010)

The following were obtained according to the process in example 1, using isopropyl 2-(4-((4-methoxybenzoyl)phenoxy)-2-methylpropionate as the raw material.

Isopropyl 2-(4-((4-methoxyphenyl)bis(ethylmercapto)methyl)phenoxy)-2-methylpropionate $^1$H NMR (400 MHz, CDCl$_3$) δ: 1.04 (t, J=6.6 Hz, 6H), 1.19 (d, J=7.2 Hz, 6H), 1.59 (s, 6H), 2.30 (q, J=6.6 Hz, 4H), 3.80 (s, 3H), 5.06-5.08 (m, 1H), 6.73 (d, J=8.4 Hz, 2H), 6.80 (d, J=7.2 Hz, 2H), 7.39 (d, J=8.8 Hz, 2H), 7.43 (d, J=6.8 Hz, 2H); ESI-MS (m/z): 485.5 (Na+H$^+$).

Isopropyl 2-(4-((4-methoxyphenyl)difluoromethyl)phenoxy)-2-methylpropionate

ESI-MS (m/z): 401.0 (M+Na$^+$), 379.0 (M+H$^+$), 417.0 (M+K$^+$).

Example 9

Isopropyl 2-(4-((3-chlorophenyl)difluoromethyl)phenoxy)-2-methylpropionate (HS003-011)

The following were obtained according to the process in example 1, using isopropyl 2-(4-((3-chlorobenzoyl)phenoxy)-2-methylpropionate as the raw material.

Isopropyl 2-(4-((3-chlorophenyl)bis(ethylmercapto) methyl)phenoxy)-2-methylpropionate $^1$H NMR (400 MHz, CDCl$_3$) δ: 1.06 (t, J=7.4 Hz, 6H), 1.19 (d, J=6 Hz, 6H), 1.60 (s, 6H), 2.31 (q, J=7.4 Hz, 4H), 5.06-5.09 (m, 1H), 6.75 (d, J=8.8 Hz, 2H), 7.15-7.23 (m, 2H), 7.33-7.45 (m, 3H), 7.51 (s, 1H); ESI-MS (m/z): 467.5 (M+H$^+$), 485.5 (M+Na$^+$).

Isopropyl 2-(4-((3-chlorophenyl)difluoromethyl) phenoxy)-2-methylpropionate $^1$H NMR (400 MHz, CDCl$_3$) δ: 1.20 (d, J=6.4 Hz, 6H), 1.61 (s, 6H), 5.04-5.10 (m, 1H), 6.84 (d, J=8.8 Hz, 2H), 7.33 (d, J=8.8 Hz, 2H), 7.36-7.41 (m, 3H), 7.47 (s, 1H); $^{13}$C NMR (100 MHz, CDCl$_3$) ppm 173.3, 157.1, 139.7 (t), 134.5, 130.1 (t), 130.0, 129.8, 127.0 (t), 126.2 (t), 124.1 (t), 120.0 (t), 118.1, 79.3, 69.2, 25.4, 21.5; ESI-MS (m/z): 405.0 (M+Na$^+$), 383.0 (M+H$^+$).

Example 10

Isopropyl 2-(4-((3-methylphenyl)difluoromethyl) phenoxy)-2-methylpropionate (HS003-012)

The following were obtained according to the process in example 1, using isopropyl 2-(4-((3-methylbenzoyl)phenoxy)-2-methylpropionate as the raw material.

Isopropyl 2-(4-((3-methylphenyl)bis(ethylmercapto) fluoromethyl)phenoxy)-2-methylpropionate $^1$H NMR (400 MHz, CDCl$_3$) δ: 1.05 (t, J=7.4 Hz, 6H), 1.19 (d, J=6.4 Hz, 6H), 1.59 (s, 6H), 2.28-2.31 (m, 7H), 5.06-5.09 (m, 1H), 6.73 (d, J=8.4 Hz, 2H), 7.02 (d, J=6.8 Hz, 1H), 7.15 (t, J=7.4 Hz, 1H), 7.28-7.33 (m, 2H), 7.39 (d, J=8.8 Hz, 2H); ESI-MS (m/z): 469.4 (M+Na$^+$).

Isopropyl 2-(4-((3-methylphenyl)difluoromethyl) phenoxy)-2-methylpropionate $^1$H NMR (400 MHz, CDCl$_3$) δ: 1.20 (d, J=6.4 Hz, 6H), 1.60 (s, 6H), 2.36 (s, 3H), 5.04-5.10 (m, 1H), 6.83 (d, J=8.8 Hz, 2H), 7.21-7.29 (m, 4H), 7.35 (d, J=8.8 Hz, 2H); $^{13}$C NMR (100 MHz, CDCl$_3$) ppm 173.4, 157.0, 138.1, 137.7 (t), 131.0 (t), 130.5, 128.2, 127.1 (t), 126.4 (t), 123.0 (t), 120.9 (t), 118.0, 79.2, 69.1, 25.4, 21.5, 21.4; ESI-MS (m/z): 385.0 (M+Na$^+$), 363.0 (M+H$^+$).

Example 11

Isopropyl 2-(4-((3-trifluoromethylphenyl)difluoromethyl)phenoxy)-2-methylpropionate (HS003-013)

The following were obtained according to the process in example 1, using isopropyl 2-(4-((3-trifluoromethylbenzoyl)phenoxy)-2-methylpropionate as the raw material.

Isopropyl 2-(4-((3-trifluoromethylphenyl)bis(ethylmercapto)methyl)phenoxy)-2-methylpropionate $^1$H NMR (400 MHz, CDCl$_3$) δ: 1.06 (t, J=7.6 Hz, 6H), 1.18 (d, J=6.4 Hz, 6H), 1.60 (s, 6H), 2.24-2.37 (m, 4H), 5.04-5.10 (m, 1H), 6.75 (d, J=8.4 Hz, 2H), 7.36-7.41 (m, 3H), 7.48 (d, J=7.4 Hz, 1H), 7.70 (d, J=7.6 Hz, 1H), 7.80 (s, 1H); ESI-MS (m/z): 523.5 (M+Na$^+$).

Isopropyl 2-(4-((3-trifluoromethylphenyl)difluoromethyl)phenoxy)-2-methylpropionate $^1$H NMR (400 MHz, CDCl$_3$) δ: 1.19 (d, J=6.4 Hz, 6H), 1.61 (s, 6H), 5.05-5.09 (m, 1H), 6.85 (d, J=9.2 Hz, 2H), 7.34 (d, J=8.8 Hz, 2H), 7.52-7.56 (m, 1H), 7.67-7.70 (m, 2H), 7.75 (s, 1H); $^{13}$C NMR (100 MHz, CDCl$_3$) ppm 173.3, 157.3, 138.9 (t), 131.1 (q), 129.8 (t), 129.3 (t), 129.1, 127.0 (t), 126.7, 125.1 (t), 122.8 (m), 120.1 (t), 118.1, 79.4, 69.2, 25.4, 21.5; ESI-MS (m/z): 439.0 (M+Na$^+$), 417.0 (M+H$^+$).

Example 12

Isopropyl 2-(4-((2-chlorophenyl)difluoromethyl) phenoxy)-2-methylpropionate (HS003-014)

The following were obtained according to the process in example 1, using isopropyl 2-(4-((2-chlorobenzoyl)phenoxy)-2-methylpropionate as the raw material.

Isopropyl 2-(4-((2-chlorophenyl)bis(ethylmercapto) methyl)phenoxy)-2-methylpropionate $^1$H NMR (400 MHz, CDCl$_3$) δ: 1.02 (t, J=7.4 Hz, 6H), 1.08 (d, J=8 Hz, 6H), 1.58 (s, 6H), 2.18-2.27 (m, 2H), 2.33-2.41 (m, 2H), 5.03-5.09 (m, 1H), 6.73 (d, J=8.8 Hz, 2H), 7.18 (d, J=8.4 Hz, 2H), 7.22-7.38 (m, 3H), 8.06 (d, J=7.2 Hz, 1H); ESI-MS (m/z): 469.5 (M+Na$^+$).

Isopropyl 2-(4-((2-chlorophenyl)difluoromethyl) phenoxy)-2-methylpropionate $^1$H NMR (400 MHz, CDCl$_3$) δ: 1.17 (d, J=6.4 Hz, 6H), 1.61 (s, 6H), 5.04-5.07 (m, 1H), 6.82 (d, J=8.8 Hz, 2H), 7.31 (d, J=8.8 Hz, 2H), 7.36-7.40 (m, 3H), 7.76-7.78 (m, 1H); $^{13}$C NMR (100 MHz, CDCl$_3$) ppm 173.4, 157.0, 134.7 (t), 132.6 (t), 131.4, 131.3, 129.7 (t), 127.8 (t), 127.2 (t), 126.6, 119.7 (t), 117.8, 79.2, 69.1, 25.4, 21.5; ESI-MS (m/z): 405.0 (M+Na$^+$), 383.0 (M+H$^+$).

Example 13

Isopropyl 2-(4-((2-methylphenyl)difluoromethyl) phenoxy)-2-methylpropionate (HS003-015)

The following were obtained according to the process in example 1, using isopropyl 2-(4-((2-methylbenzoyl)phenoxy)-2-methylpropionate as the raw material.

Isopropyl 2-(4-((2-methylphenyl)bis(ethylmercapto) methyl)phenoxy)-2-methylpropionate $^1$H NMR (400 MHz, CDCl$_3$) δ: 1.00 (t, J=7.4 Hz, 6H), 1.19 (d, J=6 Hz, 6H), 1.58 (s, 6H), 1.86 (s, 3H), 2.19-2.25 (m, 2H), 2.31-2.39 (m, 2H), 5.06-5.10 (m, 1H), 6.72 (d, J=8 Hz, 2H), 7.07-7.20 (m, 5H), 7.96 (s, 1H); ESI-MS (m/z): 447.5 (M+H$^+$), 469.5 (M+Na$^+$).

Isopropyl 2-(4-((2-methylphenyl)difluoromethyl) phenoxy)-2-methylpropionate $^1$H NMR (400 MHz, CDCl$_3$) δ: 1.18 (d, J=6.4 Hz, 6H), 1.60 (s, 6H), 2.18 (s, 3H), 5.03-5.08 (m, 1H), 6.82 (d, J=9.2 Hz, 2H), 7.20 (d, J=7.6 Hz, 1H), 7.24-7.36 (m, 4H), 7.57 (d, J=7.6 Hz, 1H); $^{13}$C NMR (100 MHz, CDCl$_3$) ppm 173.4, 156.9, 136.2 (t), 135.2 (t), 131.8, 130.5 (t), 130.0, 127.3 (t), 126.4 (t), 125.5, 121.3, 117.9, 79.2, 69.2, 25.3, 21.5; ESI-MS (m/z): 385.1 (M+Na$^+$), 363.0 (M+H$^+$).

Example 14

Isopropyl 2-(4-((2-trifluoromethylphenyl)difluoromethyl)phenoxy)-2-methylpropionate (HS003-016)

The following were obtained according to the process in example 1, using isopropyl 2-(4-((2-trifluoromethylbenzoyl)phenoxy)-2-methylpropionate as the raw material.

Isopropyl 2-(4-((2-trifluoromethylphenyl)bis(ethylmercapto)methyl)phenoxy)-2-methylpropionate $^1$H NMR (400 MHz, CDCl$_3$) δ: 1.02 (t, J=7.6 Hz, 6H), 1.19 (d, J=6.4 Hz, 6H), 1.59 (s, 6H), 2.17-2.24 (m, 2H), 2.34-2.40 (m, 2H), 5.04-5.08 (m, 1H), 6.71 (d, J=8.8 Hz, 2H), 7.15 (d, J=8.8 Hz, 2H), 7.45 (t, J=7.6 Hz, 1H), 7.56 (t, J=7.2 Hz, 1H), 7.71 (d, J=7.6 Hz, 1H), 8.28 (d, J=8.0 Hz, 1H); ESI-MS (m/z): 501.5 (M+H$^+$), 523.5 (M+Na$^+$).

Isopropyl 2-(4-((2-trifluoromethylphenyl)difluoromethyl)phenoxy)-2-methylpropionate $^1$H NMR (400 MHz, CDCl$_3$) δ: 1.17 (d, J=6.4 Hz, 6H), 1.60 (s, 6H), 5.02-5.08 (m, 1H), 6.80 (d, J=8.8 Hz, 2H), 7.25 (d, J=8.4 Hz, 2H), 7.57-7.66 (m, 2H), 7.75 (d, J=7.6 Hz, 1H), 7.81 (d, J=7.6 Hz, 1H); $^{13}$C NMR (100 MHz, CDCl$_3$) ppm 173.4, 157.1, 135.0 (t), 131.6, 130.6 (t), 130.2, 128.9 (t), 127.7 (q), 127.1 (t), 124.7, 122.0, 120.2 (t), 117.8, 79.3, 69.1, 25.4, 21.5; ESI-MS (m/z): 439.1 (M+Na$^+$), 417.1 (M+H$^+$).

Example 15

Isopropyl 2-(4-((4-methoxyacylphenyl)difluoromethyl)phenoxy)-2-methylpropionate (HS003-017)

The following were obtained according to the process in example 1, using isopropyl 2-(4-((4-methoxyacylbenzoyl)phenoxy)-2-methylpropionate as the raw material.

Isopropyl 2-(4-((4-methoxyacylphenyl)bis(ethylmercapto)methyl)phenoxy)-2-methylpropionate $^1$H NMR (400 MHz, CDCl$_3$) δ: 1.05 (t, J=7.2 Hz, 6H), 1.19 (d, J=6 Hz, 6H), 1.25 (s, 3H), 1.60 (s, 6H), 2.30 (q, J=7.2 Hz, 4H), 3.91 (s, 3H), 5.06-5.19 (m, 1H), 6.74 (d, J=8.8 Hz, 2H), 7.36 (d, J=8.4 Hz, 2H), 7.59 (d, J=8.4 Hz, 2H), 7.94 (d, J=8.0 Hz, 2H); ESI-MS (m/z): 513.5 (M+Na$^+$).

Isopropyl 2-(4-((4-methoxyacylphenyl)difluoromethyl)phenoxy)-2-methylpropionate $^1$H NMR (400 MHz, CDCl$_3$) δ: 1.19 (d, J=6 Hz, 6H), 1.60 (s, 6H), 3.93 (s), 5.05-5.08 (m, 1H), 6.83 (d, J=8.8 Hz, 2H), 7.33 (d, J=8.4 Hz, 2H), 7.57 (d, J=8.0 Hz, 2H), 8.08 (d, J=8.0 Hz, 2H); $^{13}$C NMR (100 MHz, CDCl$_3$) ppm 173.3, 166.3, 157.1, 142.1 (t), 131.5, 130.2 (t), 129.7, 126.9 (t), 125.9 (t), 120.3 (t), 118.1, 79.3, 69.1, 52.3, 25.4, 21.5; ESI-MS (m/z): 429.1 (M+Na$^+$), 407.1 (M+H$^+$).

Example 16

Bis-(isopropyl 2-methylpropionate-2-oxyphenyl-4-)-difluoromethane (HS003-018)

The following were obtained according to the process in example 1, using 4,4'-(isopropyl 2-methylpropionate-2-oxy)-dibenzophenone as the raw material.

bis-(isopropyl 2-methylpropionate-2-oxyphenyl-4-)-bis(ethylmercapto)methane $^1$H NMR (400 MHz, CDCl$_3$) δ: 1.03 (t, J=7.6 Hz, 6H), 1.21 (d, J=6.4 Hz, 12H), 1.61 (s, 12H), 2.29 (q, J=7.6 Hz, 4H), 5.07-5.10 (m, 1H), 6.74 (d, J=8.8 Hz, 4H), 7.37 (d, J=8 Hz, 4H); ESI-MS (m/z): 599.6 (M+Na$^+$).

bis-(isopropyl 2-methylpropionate-2-oxyphenyl-4-)-difluoromethane $^1$H NMR (400 MHz, CDCl$_3$) δ: 1.20 (d, J=6.4 Hz, 12H), 1.60 (s, 12H), 5.04-5.10 (m, 2H), 6.82 (d, J=8.4 Hz, 4H), 7.32 (d, J=8.8 Hz, 4H); $^{13}$C NMR (100 MHz, CDCl$_3$) ppm 173.4, 156.8, 131.8, 127.1 (t), 117.9, 117.2, 79.3, 69.2, 25.4, 21.5; ESI-MS (m/z): 515.1 (M+Na$^+$), 493.1 (M+H$^+$).

Example 17

Isopropyl 2-(4-((4-chlorophenyl)difluoromethyl)-3-methylphenoxy)-2-methylpropionate (HS003-019)

The following were obtained according to the process in example 1, using isopropyl 2-(4-((4-chlorobenzoyl)-3-methylphenoxy)-2-methylpropionate as the raw material.

Isopropyl 2-(4-((4-chlorophenyl)bis(ethylmercapto)methyl)-3-methylphenoxy)-2-methylpropionate $^1$H NMR (400 MHz, CDCl$_3$) δ: 1.03 (t, J=7.6 Hz, 6H), 1.23 (d, J=6 Hz, 6H), 1.63 (s, 6H), 1.83 (s, 3H), 2.19-2.35 (m, 4H), 5.09-5.15 (m, 1H), 6.64-6.66 (m, 2H), 7.21-7.29 (m, 4H), 7.82 (d, J=8.4 Hz, 1H); ESI-MS (m/z): 503 (M+Na$^+$).

Isopropyl 2-(4-((4-chlorophenyl)difluoromethyl)-3-methylphenoxy)-2-methylpropionate $^1$H NMR (400 MHz, CDCl$_3$) δ: 1.21 (d, J=6.4 Hz, 6H), 1.64 (s, 6H), 2.14 (s, 3H), 5.09 (m, 1H), 6.66 (d, J=8.8 Hz, 1H), 6.70 (s, 1H), 7.33-7.37 (m, 5H); $^{13}$C NMR (100 MHz, CDCl$_3$) ppm 173.4, 157.0, 138.1, 136.2 (t), 136.0, 128.8, 128.6, 127.8 (t), 127.6 (t), 121.8 121.0 (t), 114.4, 79.1, 69.1, 25.4, 21.5, 20.3; ESI-MS (m/z): 397.0 (M+H$^+$).

Example 18

Isopropyl 2-(4-((4-chlorophenyl)difluoromethyl)-2-chlorophenoxy)-2-methylpropionate (HS003-020)

The following were obtained according to the process in example 1, using isopropyl 2-(4-((4-chlorobenzoyl)-2-chlorophenoxy)-2-methylpropionate as the material.

Isopropyl 2-(4-((4-chlorophenyl)bis(ethylmercapto)methyl)-2-chlorophenoxy)-2-methylpropionate $^1$H NMR (400 MHz, CDCl$_3$) δ: 1.09 (t, J=7.4 Hz, 6H), 1.23 (d, J=6 Hz, 6H), 1.63 (s, 6H), 2.32 (q, J=7.4 Hz, 4H), 5.08-5.11 (m, 1H), 6.79 (d, J=8.8 Hz, 1H), 7.26-7.29 (m, 3H), 7.47 (d, J=8.0 Hz, 2H), 7.55 (s, 1H); ESI-MS (m/z): 523.0 (M+Na$^+$).

Isopropyl 2-(4-((4-chlorophenyl)difluoromethyl)-2-chlorophenoxy)-2-methylpropionate $^1$H NMR (400 MHz, CDCl$_3$) δ: 1.22 (d, J=6 Hz, 6H), 1.63 (s, 6H), 5.05-5.11 (m, 1H), 6.86 (d, J=8.8 Hz, 2H), 7.20-7.22 (m, 1H), 7.39-7.43 (m, 4H), 7.48 (s, 1H); $^{13}$C NMR (100 MHz, CDCl$_3$) ppm 173.0, 153.1, 136.3, 136.0 (t), 131.6 (t), 128.8, 128.2 (t), 127.3 (t), 126.1, 124.8 (t), 119.7 (t), 118.3, 81.0, 69.3, 25.2, 21.5; ESI-MS (m/z): 439.0 (M+Na$^+$), 417.0 (M+H$^+$).

Example 19

Benzyl 2-(4-((4-chlorophenyl)difluoromethyl)phenoxy)-acetate (HS003-021)

The following were obtained according to the process in example 1, using benzyl 2-(4-((4-chlorobenzoyl) phenoxy) acetate as the raw material.

Benzyl 2-(4-((4-chlorophenyl)bis(ethylmercapto)methyl)phenoxy)-acetate $^1$H NMR (400 MHz, CDCl$_3$) δ: 1.10 (t, J=7.4 Hz, 6H), 2.33 (q, J=7.4 Hz, 4H), 4.68 (s, 2H), 5.27 (s, 2H), 6.83 (d, J=8.8 Hz, 2H), 7.28 (d, J=8.8 Hz, 2H), 7.37-7.38 (m, 5H), 7.44-7.50 (m, 4H); ESI-MS (m/z): 509.0 (M+Na$^+$).

Benzyl 2-(4-((4-chlorophenyl)difluoromethyl)phenoxy)acetate $^1$H NMR (400 MHz, CDCl$_3$) δ: 4.68 (s, 2H), 5.23 (s, 2H), 6.93 (d, J=8.4 Hz, 2H), 7.36-7.46 (m, 11H); $^{13}$C NMR (100 MHz, CDCl$_3$) ppm 168.4, 159.0, 136.3 (t), 136.1, 135.0, 130.6 (t), 128.7, 128.5, 127.5 (t), 127.4 (t), 120.3 (t), 114.5, 67.2, 65.3; ESI-MS (m/z): 425.0 (M+Na$^+$), 403.0 (M+H$^+$), 441.0 (M+K$^+$).

Example 20

Ethyl 2-(4-((4-chlorophenyl)difluoromethyl)phenoxy)butyrate (HS003-023)

The following were obtained according to the process in example 1, using ethyl 2-(4-((4-chlorobenzoyl)phenoxy) butyrate as the raw material.

Ethyl 2-(4-((4-chlorophenyl)bis(ethylmercapto)methyl)phenoxy)butyrate $^1$H NMR (400 MHz, CDCl$_3$) δ: 1.07-1.11 (m, 9H), 1.26 (t, J=6.4 Hz, 3H), 1.96-2.04 (m, 2H), 2.32 (q, J=6.4 Hz, 4H), 4.21-4.27 (m, 2H), 4.55 (t, J=6.4 Hz, 1H), 6.80 (d, J=8.8 Hz, 2H), 7.26 (d, J=8.8 Hz, 2H), 7.42 (d, J=8.8 Hz, 2H), 7.48 (d, J=8.8 Hz, 2H); ESI-MS (m/z): 475.0 (M+Na$^+$).

Ethyl 2-(4-((4-chlorophenyl)difluoromethyl)phenoxy)butyrate $^1$H NMR (400 MHz, CDCl$_3$) δ: 1.07 (t, J=7.2 Hz, 3H), 1.24 (t, J=7.2 Hz, 3H), 2.00 (m, 2H), 4.21 (q, J=7.2 Hz, 2H), 4.57 (t, J=6.4 Hz, 1H), 6.90 (d, J=8.4 Hz, 2H), 7.39-7.46 (m, 6H); $^{13}$C NMR (100 MHz, CDCl$_3$) ppm 171.2, 159.2, 136.3 (t), 136.0, 130.2 (t), 128.6, 127.5 (t), 127.4 (t), 120.4 (t), 114.8, 61.3, 26.1, 14.2, 9.6; ESI-MS (m/z): 391.0 (M+Na$^+$), 369.0 (M+H$^+$).

Example 21

Methyl 2-(4-((4-chlorophenyl)difluoromethyl)phenoxy) propionate (HS003-024)

The following were obtained according to the process in example 1, using methyl 2-(4-((4-chlorobenzoyl)phenoxy) propionates the raw material.

Methyl 2-(4-((4-chlorophenyl)bis(ethylmercapto)methyl)phenoxy) propionate $^1$H NMR (400 MHz, CDCl$_3$) δ: 1.08 (t, J=7.4 Hz, 6H), 1.63 (d, J=6.4 Hz, 3H), 2.32 (q, J=7.4 Hz, 4H), 3.78 (s, 3H), 4.77 (q, J=8.4 Hz, 1H), 6.80 (d, J=9.2 Hz, 2H), 7.27 (d, J=8.4 Hz, 2H), 7.43 (d, J=9.2 Hz, 2H), 7.64 (d, J=8.4 Hz, 2H); ESI-MS (m/z): 477 (M+Na$^+$).

Methyl 2-(4-((4-chlorophenyl)difluoromethyl)phenoxy) propionate $^1$H NMR (400 MHz, CDCl$_3$) δ: 1.63 (d, J=6.4 Hz, 3H), 3.76 (s, 3H), 4.78 (q, J=6.8 Hz, 1H), 6.88 (d, J=8.4 Hz, 2H), 7.37-7.43 (m, 6H); $^{13}$C NMR (100 MHz, CDCl$_3$) ppm 172.2, 158.8, 136.3 (t), 136.0, 130.3 (t), 128.7, 127.5 (t), 127.4 (t), 120.4 (t), 114.8, 72.5, 52.4, 18.5; ESI-MS (m/z): 363 (M+Na$^+$), 341 (M+H$^+$).

Example 22

Ethyl 4-(4-((4-chlorophenyl)difluoromethyl)phenoxy)butyrate (HS003-026)

The following were obtained according to the process in example 1, using ethyl 2-(4-((4-chlorobenzoyl)phenoxy) butyrate as the raw material.

Ethyl 4-(4-((4-chlorophenyl)bis(ethylmercapto)methyl)phenoxy)butyrate $^1$H NMR (400 MHz, CDCl$_3$) δ: 1.10 (t, J=7.4 Hz, 6H), 1.29 (t, J=7.2 Hz, 3H), 2.21-2.14 (m, 2H), 2.33 (q, J=7.4 Hz, 4H), 2.53 (q, J=7.2 Hz, 2H), 4.02 (t, J=6 Hz, 2H), 4.16 (q, J=7.4 Hz, 2H), 6.81 (d, J=9.2 Hz, 2H), 7.26 (d, J=8.8 Hz, 2H), 7.43 (d, J=9.2 Hz, 2H), 7.49 (d, J=8.8 Hz, 2H); ESI-MS (m/z): 475.0 (M+Na$^+$).

Ethyl 2-(4-((4-chlorophenyl)difluoromethyl)phenoxy) butyrate $^1$H NMR (400 MHz, CDCl$_3$) δ: 1.26 (t, J=7.2 Hz, 3H), 2.11-2.17 (m, 2H), 2.51 (t, J=7.6 Hz, 2H), 4.02 (t, J=6 Hz, 2H), 4.15 (q, J=7.2 Hz, 2H), 6.99 (d, J=8.8 Hz, 2H), 7.36-7.44 (m, 6H); $^{13}$C NMR (100 MHz, CDCl$_3$) ppm 173.1, 160.1, 136.4 (t), 135.9, 129.5 (t), 128.6, 127.4 (t), 127.3 (t), 120.5 (t), 114.3, 66.9, 60.5, 30.7, 24.5, 14.2; ESI-MS (m/z): 391.0 (M+Na$^+$), 369.0 (M+H$^+$).

Example 23

3-(4-((4-chlorophenyl)difluoromethyl)phenoxy)-dihydrofuran-2(3H)-one (HS003-029)

The following were obtained according to the process in example 1, using 3-(4-((4-chlorobenzoyl)phenoxy)-dihydrofuran-2(3H)-one as the raw material.
$^1$H NMR (400 MHz, CDCl$_3$) δ: 1.10 (t, J=7.6 Hz, 6H), 2.33 (q, J=7.6 Hz, 4H), 2.44-2.56 (m, 1H), 2.70-2.78 (m, 1H), 4.35-4.41 (m, 1H), 4.51-4.57 (m, 1H), 4.97 (t, J=7.8 Hz, 1H), 6.97 (d, J=8.8 Hz, 2H), 7.27 (d, J=8.8 Hz, 2H), 7.45-7.51 (m, 4H); ESI-MS (m/z): 445 (M+Na$^+$).

3-(4-((4-chlorophenyl)difluoromethyl)phenoxy)-dihydrofuran-2(3H)-one $^1$H NMR (400 MHz, CDCl$_3$) δ: 2.43-2.52 (m, 1H), 2.68-2.76 (m, 1H), 4.33-4.40 (m, 1H), 4.50-4.55 (m, 1H), 4.98 (t, J=7.6 Hz, 1H), 7.06 (d, J=8.8 Hz, 2H), 7.37-7.43 (m, 6H); $^{13}$C NMR (100 MHz, CDCl$_3$) ppm 173.0, 158.4, 136.1 (t), 136.0, 130.6 (t), 128.6, 127.5 (t), 127.3 (t), 120.3 (t), 115.6, 72.3, 65.3, 29.7; ESI-MS (m/z): 361.0 (M+Na$^+$), 339.0 (M+H$^+$).

Example 24

Preparation of sodium 2-(4-((4-chlorophenyl)difluoromethyl)phenoxy)-2-methylpropionate (HS003-027)

It is obtained by the reaction between isopropyl 2-(4-((4-chlorophenyl)difluoromethyl)phenoxy)-2-methylpropionate and 10% NaOH in ethanol while stirring.
$^1$H NMR (400 MHz, CDCl$_3$) δ: 1.41 (s, 6H), 6.86 (d, J=8.8 Hz, 2H), 7.24 (d, J=8.8 Hz, 2H), 7.51-7.58 (m, 4H); $^{13}$C NMR (100 MHz, CDCl$_3$) ppm 176.3, 159.1, 136.8 (t), 135.3, 129.3, 127.8 (t), 127.5 (t), 126.5 (t), 121.3 (t), 117.7, 81.2, 26.6.

Example 25

Preparation of 2-(4-((4-chlorophenyl)difluoromethyl)phenoxy)-2-methylpropionic acid (HS003-028)

It is obtained from the solution of sodium 2-(4-((4-chlorophenyl)difluoromethyl)phenoxy)-2-methylpropionate (example 24) in ethanol, by regulating pH to 4 with 1M HCl.
ESI-MS (m/z): 363.0 (M+Na$^+$), 341.0 (M+H$^+$).

Example 26

Preparation of methyl 2-(4-((4-chlorophenyl)difluoromethyl)phenoxy)-4-hydroxy-butyrate (HS003-031)

It is prepared from HS003-029 (example 23) by heating to reflux in methanol.
$^1$H NMR (400 MHz, CDCl$_3$) δ: 2.21-2.25 (m, 2H), 3.78 (s, 3H), 3.84-3.93 (m, 2H), 4.93 (t, J=6 Hz, 1H), 6.92 (d, J=8.4 Hz, 2H), 7.39-7.45 (m, 6H); $^{13}$C NMR (100 MHz, CDCl$_3$) ppm 171.8, 158.9, 136.3 (t), 136.0, 130.6 (t), 128.7, 127.5 (t), 127.4 (t), 120.3 (t), 114.9, 73.7, 58.3, 52.4, 35.3; ESI-MS (m/z): 393.0 (M+Na$^+$), 371.0 (M+H$^+$).

Example 27

Isopropyl 2-(4-((4-chlorophenyl)difluoromethyl)-2-bromophenoxy)-2-methyl propionate (HS003-030)

$^1$H NMR (400 MHz, CDCl$_3$) δ: 1.21 (d, J=6 Hz, 6H), 1.64 (s, 6H), 5.05-5.9 (m, 1H), 6.82 (d, J=8.4 Hz, 2H), 7.24-7.26 (m, 1H), 7.40-7.43 (m, 4H), 7.65 (s, 1H); $^{13}$C NMR (100 MHz, CDCl$_3$) ppm 173.0, 154.1, 136.3, 136.0 (t), 131.6 (t), 128.8, 128.2 (t), 127.3 (t), 126.1, 124.8 (t), 119.7 (t), 118.3, 81.0, 69.3, 25.2, 21.5; ESI-MS (m/z): 463.1 (M+H$^+$).

Example 28

Isopropyl 2-(4-((4-trifluoromethylphenyl)difluoromethyl)-2-bromophenoxy)-2-methyl propionate (HS003-032)

$^1$H NMR (400 MHz, CDCl$_3$) δ: 1.21 (d, J=6.4 Hz, 6H), 1.64 (s, 6H), 5.05-5.11 (m, 1H), 6.83 (d, J=8.4 Hz, 1H), 7.24-7.27 (m, 1H), 7.62 (d, J=8 Hz, 2H), 7.67-7.71 (m, 3H); ESI-MS (m/z): 495.1 (M+H$^+$).

Example 29

Isopropyl 2-(4-((4-methoxyacylphenyl)difluoromethyl)-2-bromophenoxy)-2-methyl propionate (HS003-033)

$^1$H NMR (400 MHz, CDCl$_3$) δ: 1.21 (d, J=6.4 Hz, 6H), 1.64 (s, 6H), 3.94 (s, 3H), 5.04-5.10 (m, 1H), 6.82 (d, J=8.8 Hz, 1H), 7.26 (d, J=8.8 Hz, 1H), 7.56 (d, J=8.4 Hz, 2H), 7.67 (s, 1H), 8.09 (d, J=8.4 Hz, 2H); $^{13}$C NMR (100 MHz, CDCl$_3$) ppm 172.9, 166.2, 154.1, 141.4 (t), 131.7 (t), 131.1 (t), 129.8, 125.9 (t), 125.5 (t), 119.5 (t), 117.8, 115.5, 81.1, 69.3, 25.2, 21.5; ESI-MS (m/z): 485.1 (M+H$^+$).

TABLE 1

| example | target compound of formula I | Intermediate of formula II |
|---|---|---|
| 1, 2 | 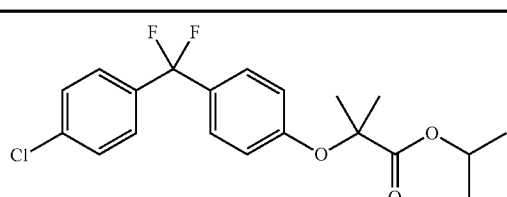<br>HS003-004 | 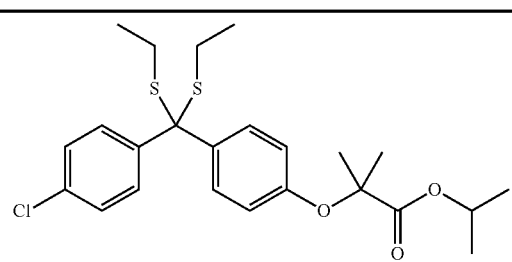 |

TABLE 1-continued

| example | target compound of formula I | Intermediate of formula II |
|---|---|---|
| 3 | HS003-005 | |
| 4 | HS003-006 | |
| 5 | HS003-007 | |
| 6 | HS003-008 | |
| 7 | HS003-009 | |
| 8 | HS003-010 | |

TABLE 1-continued
| example | target compound of formula I | Intermediate of formula II |
|---|---|---|
| 9 | 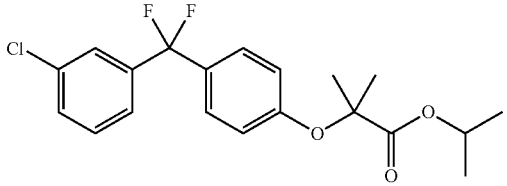 [SMILES: CC(C)OC(=O)C(C)(C)Oc1ccc(C(F)(F)c2cccc(Cl)c2)cc1] HS003-011 | 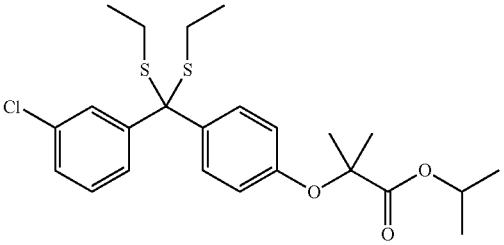 [SMILES: CCSC(SCC)(c1ccc(OC(C)(C)C(=O)OC(C)C)cc1)c1cccc(Cl)c1] |
| 10 | 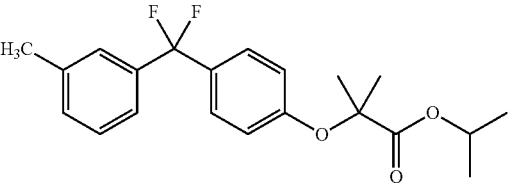 HS003-012 | 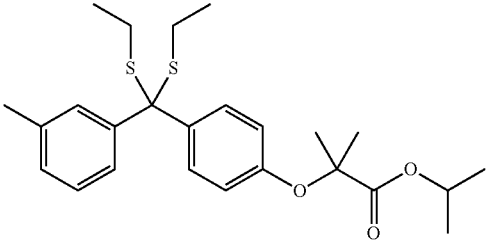 [SMILES: CCSC(SCC)(c1ccc(OC(C)(C)C(=O)OC(C)C)cc1)c1cccc(C)c1] |
| 11 | 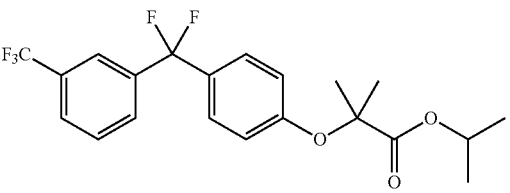 [SMILES: CC(C)OC(=O)C(C)(C)Oc1ccc(C(F)(F)c2cccc(C(F)(F)F)c2)cc1] HS003-013 | 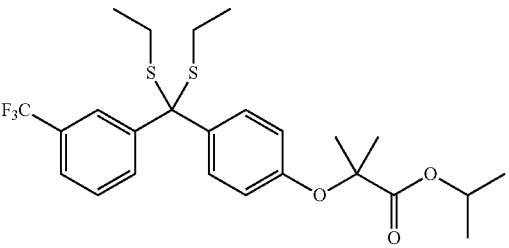 [SMILES: CCSC(SCC)(c1ccc(OC(C)(C)C(=O)OC(C)C)cc1)c1cccc(C(F)(F)F)c1] |
| 12 | 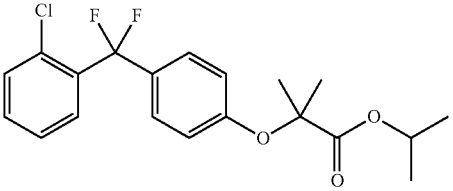 [SMILES: CC(C)OC(=O)C(C)(C)Oc1ccc(C(F)(F)c2ccccc2Cl)cc1] HS003-014 | 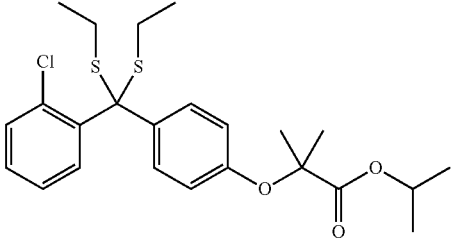 [SMILES: CCSC(SCC)(c1ccc(OC(C)(C)C(=O)OC(C)C)cc1)c1ccccc1Cl] |
| 13 | 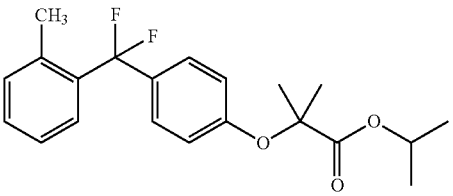 [SMILES: Cc1ccccc1C(F)(F)c1ccc(OC(C)(C)C(=O)OC(C)C)cc1] HS003-015 | 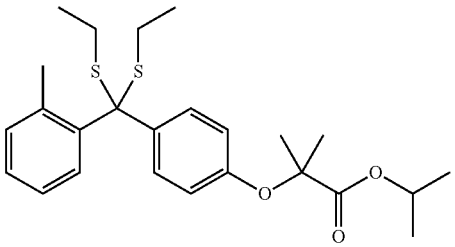 [SMILES: CCSC(SCC)(c1ccc(OC(C)(C)C(=O)OC(C)C)cc1)c1ccccc1C] |
| 14 | 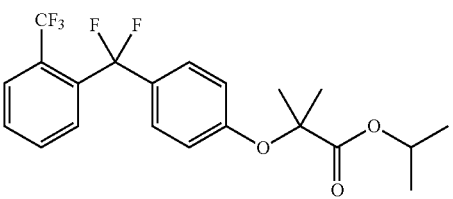 [SMILES: CC(C)OC(=O)C(C)(C)Oc1ccc(C(F)(F)c2ccccc2C(F)(F)F)cc1] HS003-016 | 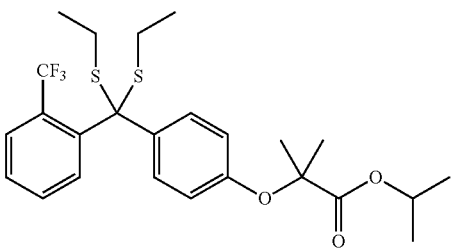 [SMILES: CCSC(SCC)(c1ccc(OC(C)(C)C(=O)OC(C)C)cc1)c1ccccc1C(F)(F)F] |

TABLE 1-continued

| example | target compound of formula I | Intermediate of formula II |
|---|---|---|
| 15 | HS003-017 | |
| 16 | HS003-018 | |
| 17 | HS003-019 | |
| 18 | HS003-020 | |
| 19 | HS003-021 | |
| 20 | HS003-023 | |

TABLE 1-continued
| example | target compound of formula I | Intermediate of formula II |
|---|---|---|
| 21 | 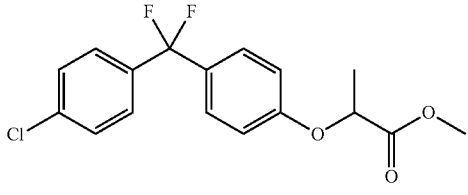 [SMILES: COC(=O)C(C)Oc1ccc(C(F)(F)c2ccc(Cl)cc2)cc1]<br>HS003-024 | 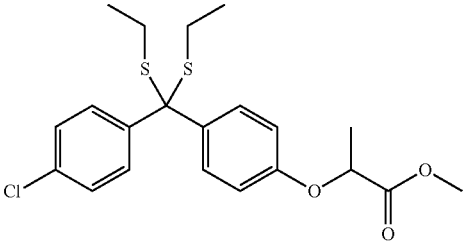 [SMILES: CCSC(SCC)(c1ccc(Cl)cc1)c1ccc(OC(C)C(=O)OC)cc1] |
| 22 | 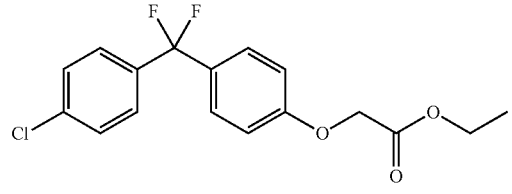 [SMILES: CCOC(=O)COc1ccc(C(F)(F)c2ccc(Cl)cc2)cc1]<br>HS003-026 | 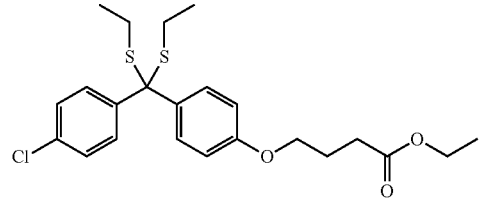 [SMILES: CCOC(=O)CCCOc1ccc(C(SCC)(SCC)c2ccc(Cl)cc2)cc1] |
| 23 | 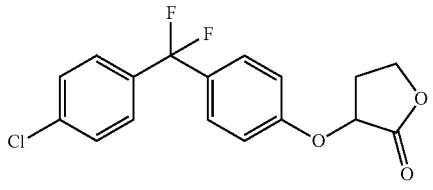 [SMILES: O=C1OCCC1Oc1ccc(C(F)(F)c2ccc(Cl)cc2)cc1]<br>HS003-029 | 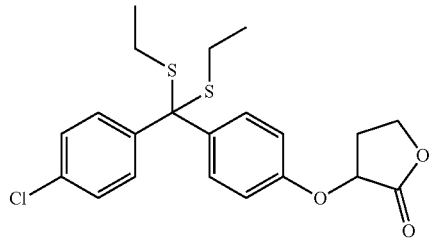 [SMILES: CCSC(SCC)(c1ccc(Cl)cc1)c1ccc(OC2CCOC2=O)cc1] |
| 24 | 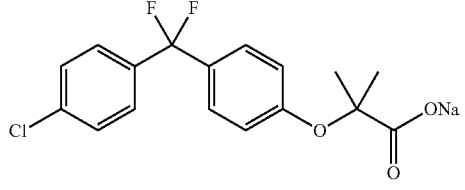<br>HS003-027 | |
| 25 | 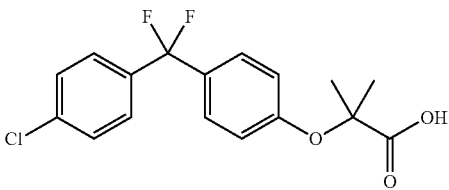 [SMILES: CC(C)(Oc1ccc(C(F)(F)c2ccc(Cl)cc2)cc1)C(=O)O]<br>HS003-028 | |
| 26 | 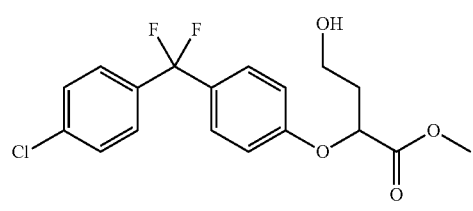 [SMILES: COC(=O)C(CCO)Oc1ccc(C(F)(F)c2ccc(Cl)cc2)cc1]<br>HS003-031 | |

TABLE 1-continued

| example | target compound of formula I | Intermediate of formula II |
|---|---|---|
| 27 | 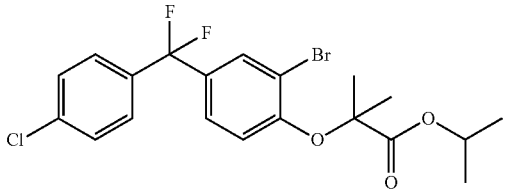 [SMILES: CC(C)OC(=O)C(C)(C)Oc1ccc(C(F)(F)c2ccc(Cl)cc2)cc1Br] HS003-030 | |
| 28 | 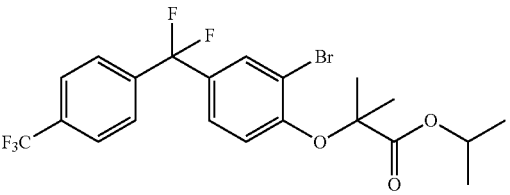 [SMILES: CC(C)OC(=O)C(C)(C)Oc1ccc(C(F)(F)c2ccc(C(F)(F)F)cc2)cc1Br] HS003-032 | |
| 29 | 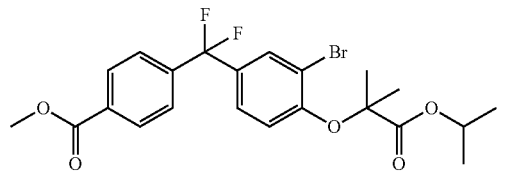 [SMILES: COC(=O)c1ccc(C(F)(F)c2ccc(OC(C)(C)C(=O)OC(C)C)c(Br)c2)cc1] HS003-033 | |

The screening of pharmacodynamics of the compounds according to the present invention was performed according to the following in vivo experiments in animals:

Example 30

Pharmacological Test Group 1

1. Materials:
Animals: 134 male Goldenhamsters, aged 8 weeks, body weight 80-100 g, provided by Vital River Laboratories, Beijing.
Drugs:
Positive control: fenofibrate
Treatment group: HS003-004, HS003-007, HS003-008, HS003-013, HS003-016, HS003-017, HS003-021, HS003-026, in the form of solids or solid powders;
HS003-006, HS003-014, HS003-020, in the form of oily liquids, all of which were provided by Shanghai Synthesis Institute of Hisun Pharmaceutical, the above drugs were insoluble in water, and the desired concentrations were formulated with 20% solutol.
Kits: The kits for total cholesterol (TC), triglyceride (TG), and high density lipoprotein cholesterol (HDL-C) were provided by SYSMEX, and the kits for low density lipoprotein cholesterol (LDL-C) were provided by Shanghai Kehua Bio-engineering Co., Ltd.
Apparatus: SYSMEX Automatic Biochemistry Analyzer, Bechman centrifuge, Setoris balance.
2. Establishing Hyperlipoidemia Model of Goldenhamsters
The animals were acclimatized and fed for 1 week, ad lib, light cycle was 10 h/14 h, and then feeds with high lipid content were fed to the animals (formulation: 0.3% cholesterol, 20% palm oil, and 79.7% basic feeds). The animals were fed for 10 days, and were fasted at 4:00 pm on the $10^{th}$ day (fasted for 16 h). On the $11^{th}$ day, the animals were anaesthetized with ethyl ether, weighted, and then 0.5 ml blood was collected from vena orbitalis posterior. The blood was anticoagulated with heparin, and was centrifugated at 5000 rpm for 10 min. The blood plasma was taken, and the levels of TC, TG, HDL-C, and LDL-C in blood plasma were determined using automatic biochemistry analyzer.
3. Screening of Compounds
The animals were acclimatized and fed for 1 week, ad lib, light cycle was 10 h/14 h, and then feeds with high lipid content were fed to the animals (formulation: 0.3% cholesterol, 20% palm oil, and 79.7% basic feeds). The animals were fed for 2 weeks, and were fasted at 4:00 pm on the $21^{st}$ day (fasted for 16 h). On the $22^{nd}$ day, the animals were anaesthetized with ethyl ether, weighted, and then 0.5 ml blood was collected from vena orbitalis posterior. The blood was anticoagulated with heparin, and was centrifugated at 5000 rpm for 10 min. The blood plasma was taken, and the levels of TC, TG, HDL-C, and LDL-C in blood plasma were determined using automatic biochemistry analyzer. The animals were classified, according to their blood lipid level and body weight, into model group, fenofibrate-40 mg/kg group, HS003-004-40 mg/kg group, HS003-006-40 mg/kg group, HS003-007-40 mg/kg group, HS003-008-40 mg/kg group, HS003-013-40 mg/kg group, HS003-014-40 mg/kg group, HS003-016-40 mg/kg group, HS003-017-40 mg/kg group, HS003-020-40 mg/kg group, HS003-021-40 mg/kg group, and HS003-026-40 mg/kg group, each group has 6 animals, and the drugs were intragastrically administered at 5 ml/kg, and the model group was administrated with equivalent volume of solvent. During the administration, feeds with high lipid content were continuously fed to the animals. The animals were fed for 1 week, and were fasted at 4:00 pm on the 7$^{th}$ day. On the 8$^{th}$ day, the animals were anaesthetized with ethyl ether, weighted, and then 0.5 ml blood was collected from vena orbitalis posterior. The blood was anticoagulated with heparin, and was centrifugated at 5000 rpm for 10 min. The blood plasma was taken, and the levels of TC, TG, HDL-C, and LDL-C in blood plasma were determined using automatic biochemistry analyzer.

4. Results of Screening

The results were represented by x̄±s, and t test was employed for comparing the results obtained before and after administration.

HS003-014 has outstanding therapeutical effects, and is significantly superior to fenofibrate; and HS003-017, HS003-021, HS003-026 tend to the effect of significantly decreasing TG and increasing HDL-C, in particular, HS003-017 and HS003-026 have outstanding therapeutic effects on decreasing TG, and are significantly superior to fenofibrate.

Example 31

Pharmacological Test Group 2

1. Materials:

Animals: 120 male Goldenhamsters, aged 8 weeks, body weight 80-100 g, provided by Vital River Laboratories, Beijing.

TABLE 2

Effects of the compounds accoding to the present invention in test group 1 on the levels of blood lipids of Goldenhamsters in a hyperlipoidemia model.

| Group | Before administration | | | | After administration | | | |
|---|---|---|---|---|---|---|---|---|
| | TC | TG | HDL-C | LDL-C | TC | TG | HDL-C | LDL-C |
| Model | 10.67 ± 1.64 | 1.62 ± 0.63 | 3.34 ± 0.29 | 1.26 ± 0.25 | 23.23 ± 3.71 | 2.62 ± 1.06 | 4.16 ± 0.46 | 5.96 ± 3.36 |
| fenofibrate | 10.70 ± 1.63 | 2.39 ± 1 | 3.16 ± 0.24 | 1.35 ± 0.25 | 10.41 ± 0.89 | 1.13 ± 0.47** | 4.11 ± 0.15*** | 1.15 ± 0.3 |
| HS003-004 | 10.70 ± 1.63 | 2.14 ± 1.06 | 3.08 ± 0.21 | 1.44 ± 0.27 | 9.16 ± 1.22* | 1.30 ± 0.23* | 3.7 ± 0.31*** | 1.27 ± 0.26 |
| HS003-006 | 10.68 ± 1.55 | 2.03 ± 1.04 | 3.28 ± 0.29 | 1.35 ± 0.4 | 8.96 ± 0.77* | 1.06 ± 0.29* | 3.64 ± 0.31* | 1.02 ± 0.27 |
| HS003-007 | 10.69 ± 1.56 | 1.85 ± 0.78 | 3.22 ± 0.24 | 1.49 ± 0.34 | 7.42 ± 0.71*** | 2.12 ± 0.43 | 2.99 ± 0.13 | 1.26 ± 0.22 |
| HS003-008 | 10.70 ± 1.51 | 2.34 ± 1.04 | 3.16 ± 0.51 | 1.42 ± 0.29 | 9.85 ± 1.48 | 1.22 ± 0.84* | 3.46 ± 0.26 | 1.0 ± 0.45* |
| HS003-013 | 10.66 ± 1.45 | 1.91 ± 0.89 | 3.25 ± 0.31 | 1.33 ± 0.21 | 8.93 ± 0.53** | 1.84 ± 0.45 | 3.12 ± 0.25 | 1.46 ± 0.46 |
| HS003-014 | 10.63 ± 1.38 | 2.10 ± 1.24 | 3.31 ± 0.32 | 1.32 ± 0.21 | 8.20 ± 0.91** | 0.92 ± 0.25* | 3.55 ± 0.4 | 0.75 ± 0.17*** |
| HS003-016 | 10.56 ± 1.22 | 1.67 ± 0.58 | 3.22 ± 0.26 | 1.14 ± 0.35 | 8.44 ± 1.12** | 1.23 ± 0.42 | 3.40 ± 0.32 | 1.0 ± 0.23 |
| HS003-017 | 10.55 ± 1.19 | 1.82 ± 0.44 | 3.05 ± 0.27 | 1.34 ± 0.31 | 11.61 ± 1.42 | 0.81 ± 0.15*** | 4.09 ± 0.18*** | 1.41 ± 0.34 |
| HS003-020 | 10.55 ± 1.16 | 1.87 ± 0.85 | 3.23 ± 0.39 | 1.50 ± 0.51 | 8.88 ± 0.44** | 1.19 ± 0.49 | 4.18 ± 0.07*** | 1.0 ± 0.35* |
| HS003-021 | 10.56 ± 1.16 | 2.14 ± 0.64 | 3.29 ± 0.41 | 1.3 ± 0.26 | 13.37 ± 3.3* | 1.1 ± 0.53** | 4.46 ± 0.23*** | 2.08 ± 0.89 |
| HS003-026 | 10.51 ± 1.1 | 2.11 ± 0.76 | 3.3 ± 0.36 | 1.34 ± 0.53 | 11.18 ± 1.6 | 0.82 ± 0.24*** | 4.13 ± 0.32*** | 1.69 ± 0.47 |

Comparison of the results obtained before and after administration,
*P <0.05,
**P <0.01,
***P <0.001.

As shown in table 2, in comparison with the results before administration, fenofibrate (40 mg/kg) significantly decreases TG (P<0.01), and increases HDL-C (*P<0.001); HS003-004-40 mg/kg significantly decreases TG, TC (*P<0.05), and increases HDL-C (***P<0.001); HS003-006-40 mg/kg significantly decreases TG, TC (*P<0.05), and increases HDL-C (*P<0.05); HS003-007-40 mg/kg can significantly decreases TC (***P<0.001); HS003-008-40 mg/kg significantly decreases TG, LDL-C (*P<0.05); HS003-013-40 mg/kg significantly decreases TC (**P<0.01); HS003-014-40 mg/kg significantly decreases TG, TC, LDL-C (*P<0.05, P<0.01, *P<0.001); HS003-016-40 mg/kg significantly decreases TC (P<0.01); HS003-017-40 mg/kg significantly decreases TG (*P<0.001); HS003-020-40 mg/kg significantly decreases TG, LDL-C (*P<0.05,P<0.01), and increase HDL-C (*P<0.001); HS003-021-40 mg/kg significantly decreases TG value (P<0.01), and significantly increases HDL-C (*P<0.01); HS003-026-40 mg/kg significantly decreases TG value (*P<0.01), and significantly increases HDL-C (*P<0.01), after administration.

According to the results in table 2, it can be concluded that all of the tested drugs has regulating effects on the levels of blood lipid in animals, in different extent. HS003-004, HS003-006, HS003-007, HS003-008, HS003-013, HS003-014, HS003-016, and HS003-020 tend to the effects of significantly decreasing TG, TC, and LDL-C, wherein Drugs: fenofibrate, HS003-004, HS003-009, HS003-011, HS003-012, HS003-014, HS003-015, HS003-019, and HS003-020, provided by Shanghai Synthesis Institute of Hisun Pharmaceutical, the above drugs were insoluble in water, and the desired concentrations were formulated with 20% solutol.

Kits: The kits for total cholesterol (TC) and high density lipoprotein cholesterol (HDL-C) were provided by SYSMEX, and the kits for low density lipoprotein cholesterol (LDL-C) were provided by Shanghai Kehua Bio-engineering Co., Ltd.

Apparatus: SYSMEX Automatic Biochemistry Analyzer, Bechman centrifuge, Setoris balance.

2. Establishing Hyperlipoidemia Model of Goldenhamsters

The animals were acclimatized and fed for 1 week, ad lib, light cycle was 10 h/14 h, and then feeds with high lipid content were fed to the animals (formulation: 0.3% cholesterol, 20% palm oil, and 79.7% basic feeds). The animals were fed for 2 weeks, and were fasted at 4:00 pm on the 14$^{th}$ day (fasted for 16 h). On the 15$^{th}$ day, the animals were anaesthetized with ethyl ether, weighted, and then 0.5 ml blood was collected from vena orbitalis posterior. The blood was anticoagulated with heparin, and was centrifugated at 5000 rpm for 10 min. The blood plasma was taken, and the levels of TC, HDL-C, and LDL-C in blood plasma were determined using automatic biochemistry analyzer.

3. Screening of Compounds

The animals were classified, according to their blood lipid level and body weight, into model group, fenofibrate-40 mg/kg group, HS003-004-40 mg/kg group, HS003-009-40 mg/kg group, HS003-011-40 mg/kg group, HS003-012-40 mg/kg group, HS003-014-40 mg/kg group, HS003-015-40 mg/kg group, HS003-019-40 mg/kg group, and HS003-020-40 mg/kg group, each group has 6 animals, and the drugs were intragastrically administered at 5 ml/kg, and the model group was administered with equivalent volume of 20% solutol. During the administration, feeds with high lipid content were continuously fed to the animals. The animals were fed for 1 week, and were fasted at 4:00 pm on the $7^{th}$ day. On the $8^{th}$ day, the animals were anaesthetized with ethyl ether, weighted, and then 0.5 ml blood was collected from vena orbitalis posterior. The blood was anticoagulated with heparin, and was centrifugated at 5000 rpm for 10 min. The blood plasma was taken, and the levels of TC, HDL-C, and LDL-C in blood plasma were determined using automatic biochemistry analyzer.

4. Result of Screening

The results were represented by $\bar{x}\pm s$, and t test was employed for comparing the results obtained before and after administration.

TABLE 3

Effects of the compounds accoding to the present invention in test group 2 on the levels of blood lipids of Goldenhamsters in hyperlipoidemia model.

| Group | Dosage (mg/kg) | Before administration | | | After administration | | |
|---|---|---|---|---|---|---|---|
| | | TC | LDL-C | HDL-C | TC | LDL-C | HDL-C |
| Model | — | 13.79 ± 2.75 | 3.07 ± 1.17 | 1.58 ± 0.16 | 19.76 ± 0.91 | 4.47 ± 1.07 | 1.64 ± 0.14 |
| Fenofibrate | 40 | 13.74 ± 2.71 | 4.24 ± 1.51 | 1.46 ± 0.29 | 11.59 ± 1.05* | 2.45 ± 0.8** | 1.92 ± 0.4* |
| HS003-004 | 40 | 13.82 ± 2.69 | 3.26 ± 1.58 | 1.61 ± 0.21 | 9.86 ± 0.83** | 1.97 ± 0.66* | 1.83 ± 0.18* |
| HS003-011 | 40 | 13.91 ± 2.34 | 4.02 ± 1.34 | 1.46 ± 0.16 | 11.94 ± 2.71 | 2.21 ± 0.91** | 1.93 ± 0.91*** |
| HS003-014 | 40 | 13.97 ± 2.27 | 3.36 ± 1.19 | 1.57 ± 0.16 | 9.51 ± 1*** | 1.39 ± 0.51** | 1.82 ± 0.18* |
| HS003-015 | 40 | 13.99 ± 2.3 | 3.14 ± 1.22 | 1.54 ± 0.07 | 15.3 ± 3.74 | 2.26 ± 1.03 | 1.77 ± 0.18* |
| HS003-019 | 40 | 13.99 ± 2.28 | 3.12 ± 1.47 | 1.67 ± 0.22 | 10.62 ± 1.02** | 1.83 ± 0.56* | 1.84 ± 0.21 |
| HS003-020 | 40 | 14.06 ± 2.17 | 3.94 ± 1.41 | 1.45 ± 0.2 | 10.34 ± 1.17** | 1.42 ± 0.39*** | 1.84 ± 0.14** |

Comparison of the results obtained before and after administration,
*P <0.05,
**P <0.01,
***P <0.001

Comparison of the results obtained before and after administration, *P<0.05, P<0.01, *P<0.001.

As shown in table 3, in comparison with the results before administration, fenofibrate (40 mg/kg) can significantly decrease the values of TC and LDL-C (*P<0.05,**P<0.01), increases the value of HDL-C (*P<0.05); HS003-004-40 mg/kg significantly decreases the values of TC and LDL-C (*P<0.05,**P<0.01), and increases the value of HDL-C (*P<0.05); HS003-011-40 mg/kg can significantly decreases the value of LDL-C (P<0.01), and increase the value of HDL-C (*P<0.001); HS003-014-40 mg/kg significantly decreases the value of TC and LDL-C (P<0.01, *P<0.001), and increases the value of HDL-C (*P<0.05); HS003-015-40 mg/kg significantly increases the value of HDL-C (*P<0.05); HS003-019-40 mg/kg significantly decreases the values of TC and LDL-C (*P<0.05, P<0.01); HS003-020-40 mg/kg significantly decreases the values of TC and LDL-C (*P<0.001, P<0.01), and significantly increases the value of HDL (P<0.01), after administration.

According to the results in table 3, it can be concluded that HS003-004, HS003-011, HS003-014, HS003-019, and HS003-020 have excellent blood lipid-regulating effects, wherein HS003-004, HS003-014, HS003-019, and HS003-020 have outstanding therapeutic effects, and are superior to fenofibrate.

Example 32

Pharmacodynamic Test Group 3

1. Materials:

Animals: 120 male Goldenhamsters, aged 8 weeks, body weight 80-100 g, provided by Vital River Laboratories, Beijing.

Drugs: fenofibrate, HS003-004, HS003-008, HS003-023, HS003-024, and HS003-031, provided by Shanghai Synthesis Institute of Hisun Pharmaceutical, the above drugs were insoluble in water, and the desired concentrations were formulated with 20% solutol.

Kits: The kits for total cholesterol (TC), triglyceride (TG), and high density lipoprotein cholesterol (HDL-C) were provided by SYSMEX, and the kits for low density lipoprotein cholesterol (LDL-C) were provided by Shanghai Kehua Bio-engineering Co., Ltd.

Apparatus: SYSMEX Automatic Biochemistry Analyzer, Bechman centrifuge, Setoris balance.

2. Establishing Hyperlipoidemia Model of Goldenhamsters

The animals were acclimatized and fed for 1 week, ad lib, light cycle was 10 h/14 h, and then feeds with high lipid content were fed to the animals (formulation: 0.3% cholesterol, 20% palm oil, and 79.7% basic feeds). The animals were fed for 2 weeks, and were fasted at 4:00 pm of the $14^{th}$ day (fasted for 16 h). At the $15^{th}$ day, the animals were anaesthetized with ethyl ether, weighted, and then 0.5 ml blood was collected from vena orbitalis posterior. The blood was anticoagulated with heparin, and was centrifugated at 5000 rpm for 10 min. The blood plasma was taken, and the levels of TC, TG, HDL-C, and LDL-C in blood plasma were determined using automatic biochemistry analyzer.

3. Screening of Compounds

The animals were classified, according to their blood lipid level and body weight, into model group, fenofibrate-40 mg/kg group, HS003-004-40 mg/kg group, HS003-008-40 mg/kg group, HS003-023-40 mg/kg group, HS003-024-40 mg/kg group, and HS003-031-40 mg/kg group, each group has 6 animals, and the drugs were intragastrically administrated at 5 ml/kg, and the model group was administrated with equivalent volume of 20% solutol. During the administration, feeds with high lipid content were continuously fed to the animals. The animals were fed for 1 week, and were fasted at 4:00 pm of the $7^{th}$ day. At the $8^{th}$ day, the animals were anaesthetized with ethyl ether, weighted, and then 0.5 ml blood was collected from vena orbitalis posterior. The blood was anticoagulated with heparin, and was centrifugated at 5000 rpm for 10 min. The blood plasma was taken, and the levels of TC, TG, HDL-C, and LDL-C in blood plasma were determined using automatic biochemistry analyzer.

4. Result of Screening

The results were represented by $\bar{x}\pm s$, and t test was employed for comparing the results obtained before and after administration.

The invention claimed is:

1. A compound of formula I, or pharmaceutically acceptable salts thereof or solvates thereof

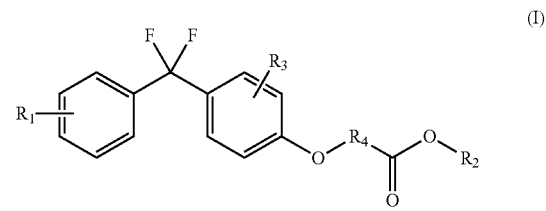

wherein, $R_1$ is hydrogen, fluoro, chloro, bromo, trifluoromethyl, substituted or unsubstituted linear or branched C1-C6 alkoxyacyl, substituted or unsubstituted C6-C10 aryloxyacyl, substituted or unsubstituted linear or branched C1-C6 alkyl, substituted or unsubstituted C6-C10 aryl, substituted or unsubstituted linear or branched C1-C6 alkoxy, substituted or unsubstituted C6-C10 aryloxy, substituted or unsubstituted linear or branched C1-C6 alkyl ester;

TABLE 4

Effects of the compounds accoding to the present invention in test group 3 on the levels of blood lipids of Goldenhamsters in a hyperlipoidemia model.

| Group | Dosage (mg/kg) | Before administration | | | | After administration | | | |
|---|---|---|---|---|---|---|---|---|---|
| | | TC | TG | HDL-C | LDL-C | TC | TG | HDL-C | LDL-C |
| Model | — | 12.89 ± 1.99 | 3.92 ± 0.96 | 2.91 ± 0.45 | 3.27 ± 0.8 | 26.43 ± 2.2 | 11.06 ± 4.08 | 3.71 ± 0.35 | 17.34 ± 4.42 |
| Fenofibrate | 40 | 12.17 ± 1.85 | 3.98 ± 1.13 | 2.57 ± 0.33 | 3.34 ± 0.24 | 10.52 ± 1.26 | 4.19 ± 1.5 | 3.38 ± 0.48** | 1.88 ± 0.92** |
| HS003-004 | 40 | 12.68 ± 1.8 | 3.94 ± 1.07 | 2.54 ± 0.22 | 3.54 ± 0.71 | 9.49 ± 1.82** | 2.22 ± 1.61* | 3.16 ± 0.24*** | 1.86 ± 0.78** |
| HS003-008 | 40 | 12.85 ± 2 | 3.93 ± 1.09 | 2.86 ± 0.14 | 3.18 ± 0.81 | 10.84 ± 1.83* | 2.49 ± 0.99* | 3.4 ± 0.11*** | 2.11 ± 0.89* |
| HS003-023 | 40 | 12.39 ± 2.38 | 3.91 ± 1.07 | 2.76 ± 0.28 | 2.86 ± 0.63 | 8.49 ± 1.08** | 2.40 ± 0.35** | 2.88 ± 0.22 | 2.26 ± 0.38* |
| HS003-024 | 40 | 12.47 ± 1.85 | 3.96 ± 1.15 | 2.76 ± 0.42 | 2.97 ± 0.98 | 7.64 ± 0.46*** | 1.92 ± 0.38*** | 2.94 ± 0.41 | 1.64 ± 0.27** |
| HS003-031 | 40 | 12.61 ± 1.66 | 4.02 ± 1.33 | 2.82 ± 0.34 | 3.2 ± 0.83 | 11.44 ± 1.05 | 1.89 ± 0.38** | 3.38 ± 0.36** | 1.94 ± 0.42** |

Comparison of the results obtained before and after administration,
*P <0.05,
**P <0.01,
***P <0.001.

As shown in table 4, in comparison with the results before administration, fenofibrate (40 mg/kg) can significantly decreases the value of LDL-C (P<0.01), and increases the value of HDL-C (P<0.01); HS003-004-40 mg/kg significantly decreases the values of TG, TC, and LDL-C (*P<0.05, P<0.01), and increases the value of HDL-C (*P<0.001); HS003-008-40 mg/kg can significantly decrease the value of TG, TC, and LDL-C (*P<0.05), and increase the value of HDL-C (***P<0.001); HS003-023-40 mg/kg significantly decreases the value of TG, TC, and LDL-C (*P<0.05, P<0.01); HS003-024-40 mg/kg significantly decreases the values of TG, TC, LDL-C (*P<0.001); HS003-031-40 mg/kg significantly decreases the values of TG and LDL-C (P<0.01), and significantly increases the value of HDL-C (P<0.01), after administration.

According to the results in table 4, it can be concluded that HS003-004, HS003-008, HS003-023, HS003-024, and HS003-031 have excellent blood lipid-regulating effects, wherein HS003-004, HS003-023, and HS003-024 have outstanding therapeutic effects, and are superior to fenofibrate.

$R_2$ is hydrogen, substituted or unsubstituted linear or branched C1-C6 alkyl, or substituted or unsubstituted C6-C10 aryl;

$R_3$ is hydrogen, fluoro, chloro, bromo, or substituted or unsubstituted linear or branched C1-C6 alkyl;

The position of $R_1$ on the benzene ring can be ortho-position, para-position or meta-position to difluoromethylene group;

The position of $R_3$ on the benzene ring can be ortho-position or meta-position to difluoromethylene group;

$R_4$ is substituted or unsubstituted C1-C6 alkyl;

$R_2$ and $R_4$ can also be cyclized together, in order to form a 5-7 membered ring, together with carbon atoms and oxygen atoms between them;

wherein, said "substituted" means being substituted with the following substituents selected from halogen, C1-C6 alkyl, C1-C6 alkoxy, C1-C6 alkenyl, C1-C6 alkynyl, C3-C6 epoxy group, hydroxyl, nitro, amino, mercapto, C1-C5 alkylamino, di(C1-C5 alkyl)amino, C1-C5 alkylmercapto, difluoromethyl, trifluoromethyl, difluoromethoxy, and carboxyl.

2. The compound according to claim 1, wherein $R_1$ is hydrogen, fluoro, chloro, bromo, trifluoromethyl, linear or branched C1-C6 alkyl, C6-C10 aryl, linear or branched C1-C6 alkoxy, C6-C10 aryloxy, linear or branched C1-C6 alkoxyacyl, C6-C10 aryloxyacyl, or linear or branched C1-C6 alkyl ester.

3. The compound according to claim 1, characterized in that $R_1$ can be selected from hydrogen, fluoro, chloro, bromo, trifluoromethyl, methyl, methoxy, methoxyacyl, or isopropyl 2-O-2-methylpropioate.

4. The compound according to claim 1, characterized in that $R_2$ can be selected from hydrogen, methyl, ethyl, propyl, isopropyl, and benzyl.

5. The compound according to claim 1, characterized in that $R_3$ can be selected from hydrogen, fluoro, chloro, bromo, methyl, and ethyl.

6. The compound according to claim 1, wherein said compound is selected from:
  isopropyl 2-(4-((4-chlorophenyl)difluoromethyl)phenoxy)-2-methylpropionate;
  isopropyl 2-(4-((4-bromophenyl)difluoromethyl)phenoxy)-2-methylpropionate;
  isopropyl-(4-((4-fluorophenyl)difluoromethyl)phenoxy)-2-methylpropionate;
  isopropyl 2-(4-((4-trifluoromethylphenyl)difluoromethyl)phenoxy)-2-methylpropionate;
  isopropyl 2-(4-(phenyldifluoromethyl)phenoxy)-2-methylpropionate;
  isopropyl 2-(4-((4-methylphenyl)difluoromethyl)phenoxy)-2-methylpropionate;
  isopropyl 2-(4-((4-methoxyphenyl)difluoromethyl)phenoxy)-2-methylpropionate;
  isopropyl 2-(4-((3-chlorophenyl)difluoromethyl)phenoxy)-2-methylpropionate;
  isopropyl 2-(4-((3-methylphenyl)difluoromethyl)phenoxy)-2-methylpropionate;
  isopropyl 2-(4-((3-trifluoromethylphenyl)difluoromethyl)phenoxy)-2-methylpropionate;
  isopropyl 2-(4-((2-chlorophenyl)difluoromethyl)phenoxy)-2-methylpropionate;
  isopropyl 2-(4-((2-methylphenyl)difluoromethyl)phenoxy)-2-methylpropionate;
  isopropyl 2-(4-((2-trifluoromethylphenyl)difluoromethyl)phenoxy)-2-methylpropionate;
  isopropyl 2-(4-((4-methoxyacylphenyl)difluoromethyl)phenoxy)-2-methylpropionate;
  bis-(isopropyl 2-methylpropionate-2-oxyphenyl-4-)-difluoromethane;
  isopropyl 2-(4-((4-chlorophenyl)difluoromethyl)-3-methylphenoxy)-2-methylpropionate;
  isopropyl 2-(4-((4-chlorophenyl)difluoromethyl)-2-chlorophenoxy)-2-methylpropionate;
  benzyl 2-(4-(4-chlorophenyl)difluoromethyl)phenoxy)-acetate;
  ethyl 2-(4-((4-chlorophenyl)difluoromethyl)phenoxy) butyrate;
  methyl 2-(4-((4-chlorophenyl)difluoromethyl)phenoxy) propionate;
  ethyl 4-(4-((4-chlorophenyl)difluoromethyl)phenoxy) butyrate;
  sodium 2-(4-((4-chlorophenyl)difluoromethyl)phenoxy)-2-methylpropionate;
  2-(4-((4-chlorophenyl)difluoromethyl)phenoxy)-2-methylpropionic acid;
  methyl 2-(4-((4-chlorophenyl)difluoromethyl)phenoxy)-4-hydroxy-butyrate;
  3-(4-((4-chlorophenyl)difluoromethyl)phenoxy)-dihydro-furan-2(3H)-one;
  isopropyl 2-(4-((4-chlorophenyl)difluoromethyl)-2-bromophenoxy)-2-methylpropionate;
  isopropyl 2-(4-((4-trifluoromethylphenyl)difluoromethyl)-2-bromophenoxy)-2-methylpropionate; and
  isopropyl 2-(4-((4-methoxyacylphenyl)difluoromethyl)-2-bromophenoxy)-2-methylpropionate.

7. A pharmaceutical composition, comprising an effective dosage of a compound of formula I according to claim 1, or a pharmaceutically acceptable salt or solvate thereof, and a pharmaceutically acceptable carrier.

8. A method of treating hyperlipoidemia comprising administering a pharmaceutical composition comprising an effective dosage of a compound of formula I according to claim 1, or a pharmaceutically acceptable salt or solvate thereof to a patient in need thereof.

9. A process for the preparation of a compound of formula I according to claim 1, comprising reacting the compound according to the following formula II with an oxidant and a fluorination reagent to obtain the compound of formula I, wherein,
$R_1$ is hydrogen, fluoro, chloro, bromo, trifluoromethyl, substituted or unsubstituted linear or branched C1-C6 alkoxyacyl, substituted or unsubstituted C6-C10 aryloxyacyl, substituted or unsubstituted linear or branched C1-C6 alkyl, substituted or unsubstituted C6-C10 aryl, substituted or unsubstituted linear or branched C1-C6 alkoxy, substituted or unsubstituted C6-C10 aryloxy, substituted or unsubstituted linear or branched C1-C6 alkyl ester;
$R_2$ is hydrogen, substituted or unsubstituted linear or branched C1-C6 alkyl, or substituted or unsubstituted C6-C10 aryl;
$R_3$ is hydrogen, fluoro, chloro, bromo, or substituted or unsubstituted linear or branched C1-C6 alkyl;
the position of $R_1$ on the benzene ring can be ortho-position, para-position or meta-position to difluoromethylene group;
the position of $R_3$ on the benzene ring can be ortho-position or meta-position to difluoromethylene group;
$R_4$ is substituted or unsubstituted C1-C6 alkyl;
$R_2$ and $R_4$ can also be cyclized together, in order to form a 5-7 membered ring, together with carbon atoms and oxygen atoms between them;
wherein, said "substituted" means being substituted with the following substituents selected from halogen, C1-C6 alkyl, C1-C6 alkoxy, C1-C6 alkenyl, C1-C6 alkynyl, C3-C6 epoxy group, hydroxyl, nitro, amino, mercapto, C1-C5 alkylamino, di(C1-C5 alkyl)amino, C1-C5 alkylmercapto, difluoromethyl, trifluoromethyl, difluoromethoxy, and carboxyl; and $R_5$ can be absent, which forms thiocarbonyl with the carbon atom between the two benzene rings, or is a substituted or unsubstituted linear or branched C1-C6 alkyl, or substituted or unsubstituted aryl, alternatively, two $R_5$ groups bond with each other and form a 5-7 member ring, together with two sulfur atoms and a carbon atom linking the two sulfur atoms.

10. The process according to claim 9, characterized in that said fluorination reagent is a nucleophilic fluorination reagent.

11. A process according to claim 10, characterized in that said nucleophilic fluorination reagent can be selected from diethylaminosulfur trifluoride, bis(2-methoxyethyl)amine-sulfur trifluoride, dimethylaminosulfur trifluoride, pyridine hydrofluoride, triethylamine hydrofluoride, sulfur tetrafluoride, hydrogen fluoride, potassium fluoride, silver fluoride, strontium fluoride, N-fluorodibenzenesulfonimide, dimethylaminosulfur trifluoride, morpholinosulfur trifluoride, 2,2-difluoro-1,3-dimethylimidazoline, 1-fluoro-2,6-dichloro-pyridine tetrafluoroborate, 1-fluoro-2,4,6-trimethylpyridine triflate, tetrabutylammonium hydrofluoride, hexafluoropropylene-diethylamine complex, difluoroiodotoluene, and N,N-diisopropylethylamine trihydrofluoride.

12. The process according to claim 9, characterized in that said oxidant can be selected from bromosuccinimide, dibromantin, iodosuccinimide, liquid bromine, or iodine.

13. A process for the preparation of the compound of formula I according to claim 1, comprising reacting the compound according to the following formula III with a fluorination reagent to obtain the compound of formula I

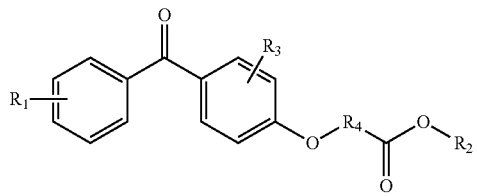

wherein,
$R_1$ is hydrogen, fluoro, chloro, bromo, trifluoromethyl, substituted or unsubstituted linear or branched C1-C6 alkoxyacyl, substituted or unsubstituted C6-C10 aryloxyacyl, substituted or unsubstituted linear or branched C1-C6 alkyl, substituted or unsubstituted C6-C10 aryl, substituted or unsubstituted linear or branched C1-C6 alkoxy, substituted or unsubstituted C6-C10 aryloxy, substituted or unsubstituted linear or branched C1-C6 alkyl ester;

$R_2$ is hydrogen, substituted or unsubstituted linear or branched C1-C6 alkyl, or substituted or unsubstituted C6-C10 aryl;

$R_3$ is hydrogen, fluoro, chloro, bromo, or substituted or unsubstituted linear or branched C1-C6 alkyl;

The position of $R_1$ on the benzene ring can be ortho-position, para-position or meta-position to difluoromethylene group;

The position of $R_3$ on the benzene ring can be ortho-position or meta-position to difluoromethylene group;

$R_4$ is substituted or unsubstituted C1-C6 alkyl;

$R_2$ and $R_4$ can also be cyclized together, in order to form a 5-7 membered ring, together with carbon atoms and oxygen atoms between them;

wherein, said "substituted" means being substituted with the following substituents selected from halogen, C1-C6 alkyl, C1-C6 alkoxy, C1-C6 alkenyl, C1-C6 alkynyl, C3-C6 epoxy group, hydroxyl, nitro, amino, mercapto, C1-C5 alkylamino, di(C1-C5 alkyl)amino, C1-C5 alkylmercapto, difluoromethyl, trifluoromethyl, difluoromethoxy, and carboxyl.

14. A compound of formula II

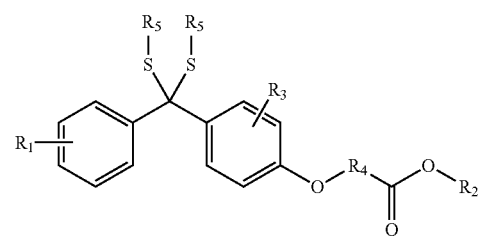

wherein
$R_1$ is hydrogen, fluoro, chloro, bromo, trifluoromethyl, substituted or unsubstituted linear or branched C1-C6 alkoxyacyl, substituted or unsubstituted C6-C10 aryloxyacyl, substituted or unsubstituted linear or branched C1-C6 alkyl, substituted or unsubstituted C6-C10 aryl, substituted or unsubstituted linear or branched C1-C6 alkoxy, substituted or unsubstituted C6-C10 aryloxy, substituted or unsubstituted linear or branched C1-C6 alkyl ester;

$R_2$ is hydrogen, substituted or unsubstituted linear or branched C1-C6 alkyl, or substituted or unsubstituted C6-C10 aryl;

$R_3$ is hydrogen, fluoro, chloro, bromo, or substituted or unsubstituted linear or branched C1-C6 alkyl;

the position of $R_1$ on the benzene ring can be ortho-position, para-position or meta-position to difluoromethylene group;

the position of $R_3$ on the benzene ring can be ortho-position or meta-position to difluoromethylene group;

$R_4$ is substituted or unsubstituted C1-C6 alkyl;

$R_2$ and $R_4$ can also be cyclized together, in order to form a 5-7 membered ring, together with carbon atoms and oxygen atoms between them;

wherein, said "substituted" means being substituted with the following substituents selected from halogen, C1-C6 alkyl, C1-C6 alkoxy, C1-C6 alkenyl, C1-C6 alkynyl, C3-C6 epoxy group, hydroxyl, nitro, amino, mercapto, C1-C5 alkylamino, di(C1-C5 alkyl)amino, C1-C5 alkylmercapto, difluoromethyl, trifluoromethyl, difluoromethoxy, and carboxyl, and $R_5$ can be absent, which forms thiocarbonyl with the carbon atom between the two benzene rings, or is a substituted or unsubstituted linear or branched C1-C6 alkyl, or substituted or unsubstituted aryl, alternatively, two $R_5$ groups bond with each other and form a 5-7 member ring, together with two sulfur atoms and a carbon atom linking the two sulfur atoms.

15. The compound of formula II according to claim 14, wherein said compound is selected from:

isopropyl 2-(4-((4-chlorophenyl)sulfurformyl)phenoxy)-2-methylpropionate;
isopropyl 2-(4-((4-chlorophenyl)bis(ethylmercapto)methyl) phenoxy)-2-methylpropionate;
isopropyl 2-(4-((4-bromophenyl)bis(ethylmercapto)methyl) phenoxy)-2-methylpropionate;
isopropyl 2-(4-((4-fluorophenyl)bis(ethylmercapto)methyl) phenoxy)-2-methylpropionate;
isopropyl 2-(4-((4-trifluoromethylphenyl)bis(ethylmercapto)methyl)phenoxy)-2-methylpropionate;
isopropyl 2-(4-(phenylbis(ethylmercapto)methyl)phenoxy)-2-methylpropionate;
isopropyl 2-(4-((4-methylphenyl)bis(ethylmercapto)methyl) phenoxy)-2-methylpropionate;
isopropyl 2-(4-((4-methoxyphenyl)bis(ethylmercapto)methyl)phenoxy)-2-methylpropionate;
isopropyl 2-(4-((3-chlorophenyl)bis(ethylmercapto)methyl)phenoxy)-2-methylpropionate;
isopropyl 2-(4-((3-methylphenyl)bis(ethylmercapto) fluoromethyl)phenoxy)-2-methylpropionate;
isopropyl 2-(4-((3-trifluoromethylphenyl)bis(ethylmercapto)methyl)phenoxy)-2-methylpropionate;
isopropyl 2-(4-((2-chlorophenyl)bis(ethylmercapto)methyl) phenoxy)-2-methylpropionate;
isopropyl 2-(4-((2-methylphenyl)bis(ethylmercapto)methyl)phenoxy)-2-methylpropionate;
isopropyl 2-(4-((2-trifluoromethylphenyl)bis(ethylmercapto)methyl)phenoxy)-2-methylpropionate;
isopropyl 2-(4-((4-methoxyacylphenyl)bis(ethylmercapto)methyl)phenoxy)-2-methylpropionate;
bis-(isopropyl 2-methylpropionate-2-oxyphenyl-4-)-bis(ethylmercapto)methane;
isopropyl 2-(4-((4-chlorophenyl)bis(ethylmercapto)methyl)-3-methylphenoxy)-2-methylpropionate;
isopropyl 2-(4-((4-chlorophenyl)bis(ethylmercapto)methyl)-2-chlorophenoxy)-2-methylpropionate;
benzyl 2-(4-((4-chlorophenyl)bis(ethylmercapto)methyl) phenoxy)-acetate;
ethyl 2-(4-((4-chlorophenyl)bis(ethylmercapto)methyl) phenoxy)butyrate;
methyl 2-(4-((4-chlorophenyl)bis(ethylmercapto)methyl) phenoxy)propionate;
ethyl 4-(4-((4-chlorophenyl)bis(ethylmercapto)methyl) phenoxy)butyrate.

16. A process for the preparation of the compound of formula II according to claim 14, comprising carrying out the following reaction between the compound of formula III and alkylthiol, arylthiol, or alkyldithiol, in the presence of a Lewis acid or a proton acid

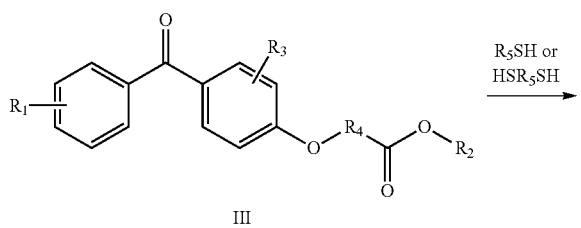

III

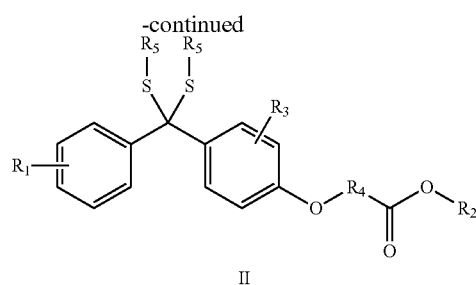

II wherein,
$R_1$ is hydrogen, fluoro, chloro, bromo, trifluoromethyl, substituted or unsubstituted linear or branched C1-C6 alkoxyacyl, substituted or unsubstituted C6-C10 aryloxyacyl, substituted or unsubstituted linear or branched C1-C6 alkyl, substituted or unsubstituted C6-C10 aryl, substituted or unsubstituted linear or branched C1-C6 alkoxy, substituted or unsubstituted C6-C10 aryloxy, substituted or unsubstituted linear or branched C1-C6 alkyl ester;
$R_2$ is hydrogen, substituted or unsubstituted linear or branched C1-C6 alkyl, or substituted or unsubstituted C6-C10 aryl;
$R_3$ is hydrogen, fluoro, chloro, bromo, or substituted or unsubstituted linear or branched C1-C6 alkyl;
the position of $R_1$ on the benzene ring can be ortho-position, para-position or meta-position to difluoromethylene group;
the position of $R_3$ on the benzene ring can be ortho-position or meta-position to difluoromethylene group;
$R_4$ is substituted or unsubstituted C1-C6 alkyl;
$R_2$ and $R_4$ can also be cyclized together, in order to form a 5-7 membered ring, together with carbon atoms and oxygen atoms between them;
said "substituted" means being substituted with the following substituents selected from halogen, C1-C6 alkyl, C1-C6 alkoxy, C1-C6 alkenyl, C1-C6 alkynyl, C3-C6 epoxy group, hydroxyl, nitro, amino, mercapto, C1-C5 alkylamino, di(C1-C5 alkyl)amino, C1-C5 alkylmercapto, difluoromethyl, trifluoromethyl, difluoromethoxy, and carboxyl; and
$R_5$ is a substituted or unsubstituted linear or branched C1-C6 alkyl, or substituted or unsubstituted aryl, alternatively, two $R_5$ groups bond with each other and form a 5-7 member ring, together with two sulfur atoms and a carbon atom linking the two sulfur atoms.

17. The process according to claim 16, characterized in that the Lewis acid can be selected from boron trifluoride etherate, chlorotrimethylsilane, zinc triflate, magnesium triflate, copper triflate, scandium triflate, bismuth nitrate, ferric trichloride, indium trichloride, zinc dichloride, titanium tetrachloride, tellurium tetrachloride, zirconium tetrachloride, and cobaltous bromide.

18. The process according to claim 16, characterized in that the proton acid can be selected from p-toluenesulfonic acid, hydrochloric acid, and sulfuric acid.

19. A process for the preparation of the compound of formula II according to claim 14, characterized in that when $R_5$ is absent, which forms thiocarbonyl with the carbon atom between the two benzene rings, the process is a reaction between the compound of formula III and Lawesson's reagent or phosphorus pentasulfide.

* * * * *